United States Patent
Morin

(10) Patent No.: US 11,813,413 B2
(45) Date of Patent: Nov. 14, 2023

(54) RADIOPAQUE OUTER CUFF FOR TRANSCATHETER VALVE

(71) Applicant: St. Jude Medical, Cardiology Division, Inc., St. Paul, MN (US)

(72) Inventor: Kristen T. Morin, St. Paul, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 380 days.

(21) Appl. No.: 16/244,226

(22) Filed: Jan. 10, 2019

(65) Prior Publication Data

US 2019/0298968 A1 Oct. 3, 2019

Related U.S. Application Data

(60) Provisional application No. 62/648,467, filed on Mar. 27, 2018.

(51) Int. Cl.
*A61M 25/01* (2006.01)
*A61F 2/24* (2006.01)

(52) U.S. Cl.
CPC ....... *A61M 25/0108* (2013.01); *A61F 2/2409* (2013.01); *A61F 2/2418* (2013.01); *A61F 2/2436* (2013.01); *A61F 2250/0098* (2013.01)

(58) Field of Classification Search
CPC .... A61F 2/2409; A61F 2/2418; A61F 2/2436; A61F 2250/0098; A61F 2/24; A61M 25/0108; A61B 17/2412; A61B 17/2418; A61B 17/2476
See application file for complete search history.

(56) References Cited

U.S. PATENT DOCUMENTS

| | | | |
|---|---|---|---|
| 3,657,744 A | 4/1972 | Ersek | |
| 4,275,469 A | 6/1981 | Gabbay | |
| 4,491,986 A | 1/1985 | Gabbay | |
| 4,759,758 A | 7/1988 | Gabbay | |
| 4,878,906 A | 11/1989 | Lindemann et al. | |

(Continued)

FOREIGN PATENT DOCUMENTS

| | | |
|---|---|---|
| AU | 2002212418 B2 | 3/2006 |
| DE | 19857887 A1 | 7/2000 |

(Continued)

OTHER PUBLICATIONS

Medical device and diagnostic industry, Radiolucent structural materials for medical applications, Jun. 2001, https://www.mddionline.com/news/radiolucent-structural-materials-medical-applications.*

(Continued)

*Primary Examiner* — Robert A Lynch
*Assistant Examiner* — Mikail A Mannan
(74) *Attorney, Agent, or Firm* — SLEMAN & LUND LLP

(57) ABSTRACT

A prosthetic heart valve for replacing a native valve includes a stent having a plurality of struts, an inflow end, an outflow end, a collapsed condition and an expanded condition. A valve assembly is disposed within the stent. A first cuff is annularly disposed adjacent the stent, and a second cuff is annularly disposed about the stent radially outward of the first cuff and radially outward of the stent. The second cuff is at least partly radiopaque and may assist in determining the relative position between the second cuff and a patient's anatomy using fluoroscopy during an implantation procedure.

7 Claims, 11 Drawing Sheets

(56) References Cited

U.S. PATENT DOCUMENTS

| | | |
|---|---|---|
| 4,922,905 A | 5/1990 | Strecker |
| 4,994,077 A | 2/1991 | Dobben |
| 5,411,552 A | 5/1995 | Andersen et al. |
| 5,415,664 A | 5/1995 | Pinchuk |
| 5,480,423 A | 1/1996 | Ravenscroft et al. |
| 5,843,167 A | 12/1998 | Dwyer et al. |
| 5,855,601 A | 1/1999 | Bessler et al. |
| 5,935,163 A | 8/1999 | Gabbay |
| 5,961,549 A | 10/1999 | Nguyen et al. |
| 6,045,576 A | 4/2000 | Starr et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,458,153 B1 | 10/2002 | Bailey et al. |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,652,578 B2 | 11/2003 | Bailey et al. |
| 6,685,625 B2 | 2/2004 | Gabbay |
| 6,716,244 B2 | 4/2004 | Klaco |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 6,951,573 B1 | 10/2005 | Dilling |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,195,641 B2 | 3/2007 | Palmaz et al. |
| 7,247,167 B2 | 7/2007 | Gabbay |
| 7,267,686 B2 | 9/2007 | DiMatteo et al. |
| 7,276,078 B2 | 10/2007 | Spenser et al. |
| 7,311,730 B2 | 12/2007 | Gabbay |
| 7,320,704 B2 | 1/2008 | Lashinski et al. |
| 7,329,278 B2 | 2/2008 | Seguin et al. |
| 7,374,573 B2 | 5/2008 | Gabbay |
| 7,381,218 B2 | 6/2008 | Schreck |
| 7,381,219 B2 | 6/2008 | Salahieh et al. |
| 7,452,371 B2 | 11/2008 | Pavcnik et al. |
| 7,510,572 B2 | 3/2009 | Gabbay |
| 7,510,575 B2 | 3/2009 | Spenser et al. |
| 7,524,331 B2 | 4/2009 | Birdsall |
| 7,534,261 B2 | 5/2009 | Friedman |
| RE40,816 E | 6/2009 | Taylor et al. |
| 7,585,321 B2 | 9/2009 | Cribier |
| 7,628,805 B2 | 12/2009 | Spenser et al. |
| 7,682,390 B2 | 3/2010 | Seguin |
| 7,708,775 B2 | 5/2010 | Rowe et al. |
| 7,731,742 B2 | 6/2010 | Schlick et al. |
| 7,748,389 B2 | 7/2010 | Salahieh et al. |
| 7,780,725 B2 | 8/2010 | Haug et al. |
| 7,799,069 B2 | 9/2010 | Bailey et al. |
| 7,803,185 B2 | 9/2010 | Gabbay |
| 7,824,442 B2 | 11/2010 | Salahieh et al. |
| 7,837,727 B2 | 11/2010 | Goetz et al. |
| 7,846,203 B2 | 12/2010 | Cribier |
| 7,846,204 B2 | 12/2010 | Letac et al. |
| 7,857,845 B2 | 12/2010 | Stacchino et al. |
| 7,892,281 B2 | 2/2011 | Seguin et al. |
| 7,914,569 B2 | 3/2011 | Nguyen et al. |
| 7,959,666 B2 | 6/2011 | Salahieh et al. |
| 7,959,672 B2 | 6/2011 | Salahieh et al. |
| 7,972,378 B2 | 7/2011 | Tabor et al. |
| 7,988,724 B2 | 8/2011 | Salahieh et al. |
| 7,993,394 B2 | 8/2011 | Hariton et al. |
| 8,016,877 B2 | 9/2011 | Seguin et al. |
| D648,854 S | 11/2011 | Braido |
| 8,048,153 B2 | 11/2011 | Salahieh et al. |
| 8,052,741 B2 | 11/2011 | Bruszewski et al. |
| 8,052,749 B2 | 11/2011 | Salahieh et al. |
| 8,052,750 B2 | 11/2011 | Tuval et al. |
| 8,062,355 B2 | 11/2011 | Figulla et al. |
| 8,075,611 B2 | 12/2011 | Millwee et al. |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| 8,137,398 B2 | 3/2012 | Tuval et al. |
| 8,142,497 B2 | 3/2012 | Friedman |
| D660,432 S | 5/2012 | Braido |
| D660,433 S | 5/2012 | Braido et al. |
| D660,967 S | 5/2012 | Braido et al. |
| 8,182,528 B2 | 5/2012 | Salahieh et al. |
| 8,221,493 B2 | 7/2012 | Boyle et al. |
| 8,230,717 B2 | 7/2012 | Matonick |
| 8,231,670 B2 | 7/2012 | Salahieh et al. |
| 8,252,051 B2 | 8/2012 | Chau et al. |
| 8,308,798 B2 | 11/2012 | Pintor et al. |
| 8,313,525 B2 | 11/2012 | Tuval et al. |
| 8,323,335 B2 | 12/2012 | Rowe et al. |
| 8,323,336 B2 | 12/2012 | Hill et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,348,998 B2 | 1/2013 | Pintor et al. |
| 8,366,769 B2 | 2/2013 | Huynh et al. |
| 8,403,983 B2 | 3/2013 | Quadri et al. |
| 8,408,214 B2 | 4/2013 | Spenser |
| 8,414,643 B2 | 4/2013 | Tuval et al. |
| 8,425,593 B2 | 4/2013 | Braido et al. |
| 8,449,599 B2 | 5/2013 | Chau et al. |
| 8,449,604 B2 | 5/2013 | Moaddeb et al. |
| D684,692 S | 6/2013 | Braido |
| 8,454,686 B2 | 6/2013 | Alkhatib |
| 8,500,798 B2 | 8/2013 | Rowe et al. |
| 8,568,474 B2 | 10/2013 | Yeung et al. |
| 8,579,962 B2 | 11/2013 | Salahieh et al. |
| 8,579,966 B2 | 11/2013 | Seguin et al. |
| 8,585,755 B2 | 11/2013 | Chau et al. |
| 8,591,575 B2 | 11/2013 | Cribier |
| 8,597,349 B2 | 12/2013 | Alkhatib |
| 8,603,159 B2 | 12/2013 | Seguin et al. |
| 8,603,160 B2 | 12/2013 | Salahieh et al. |
| 8,613,765 B2 | 12/2013 | Bonhoeffer et al. |
| 8,623,074 B2 | 1/2014 | Ryan |
| 8,652,204 B2 | 2/2014 | Quill et al. |
| 8,663,322 B2 | 3/2014 | Keranen |
| 8,668,733 B2 | 3/2014 | Haug et al. |
| 8,685,080 B2 | 4/2014 | White |
| 8,728,154 B2 | 5/2014 | Alkhatib |
| 8,747,459 B2 | 6/2014 | Nguyen et al. |
| 8,764,820 B2 | 7/2014 | Dehdashtian et al. |
| 8,795,357 B2 | 8/2014 | Yohanan et al. |
| 8,801,776 B2 | 8/2014 | House et al. |
| 8,808,356 B2 | 8/2014 | Braido et al. |
| 8,828,078 B2 | 9/2014 | Salahieh et al. |
| 8,834,563 B2 | 9/2014 | Righini |
| 8,840,661 B2 | 9/2014 | Manasse |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,940,040 B2 | 1/2015 | Shahriari |
| 8,945,209 B2 | 2/2015 | Bonyuet et al. |
| 8,961,595 B2 | 2/2015 | Alkhatib |
| 8,974,523 B2 | 3/2015 | Thill et al. |
| 8,974,524 B2 | 3/2015 | Yeung et al. |

(56) References Cited

U.S. PATENT DOCUMENTS

| | | |
|---|---|---|
| 9,687,593 B2 | 6/2017 | Vaz et al. |
| 2002/0036220 A1 | 3/2002 | Gabbay |
| 2002/0193871 A1 | 12/2002 | Beyersdorf et al. |
| 2003/0023303 A1 | 1/2003 | Palmaz et al. |
| 2003/0050694 A1 | 3/2003 | Yang et al. |
| 2003/0130726 A1 | 7/2003 | Thorpe et al. |
| 2004/0049262 A1 | 3/2004 | Obermiller et al. |
| 2004/0064014 A1* | 4/2004 | Melvin ............... A61F 2/2487 600/37 |
| 2004/0093075 A1 | 5/2004 | Kuehne |
| 2004/0111111 A1 | 6/2004 | Lin |
| 2004/0210304 A1 | 10/2004 | Seguin et al. |
| 2004/0260389 A1 | 12/2004 | Case et al. |
| 2005/0096726 A1 | 5/2005 | Sequin et al. |
| 2005/0137682 A1 | 6/2005 | Justino |
| 2005/0137695 A1 | 6/2005 | Salahieh et al. |
| 2005/0137697 A1 | 6/2005 | Salahieh et al. |
| 2005/0203605 A1 | 9/2005 | Dolan |
| 2005/0240200 A1 | 10/2005 | Bergheim |
| 2005/0256566 A1 | 11/2005 | Gabbay |
| 2006/0008497 A1 | 1/2006 | Gabbay |
| 2006/0074484 A1 | 4/2006 | Huber |
| 2006/0122692 A1 | 6/2006 | Gilad et al. |
| 2006/0149360 A1 | 7/2006 | Schwammenthal et al. |
| 2006/0161249 A1 | 7/2006 | Realyvasquez et al. |
| 2006/0173532 A1 | 8/2006 | Flagle et al. |
| 2006/0178740 A1 | 8/2006 | Stacchino et al. |
| 2006/0195180 A1 | 8/2006 | Kheradvar et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2006/0276874 A1 | 12/2006 | Wilson et al. |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0099653 A1 | 4/2009 | Suri et al. |
| 2009/0112309 A1 | 4/2009 | Jaramillo et al. |
| 2009/0138079 A1 | 5/2009 | Tuval et al. |
| 2009/0276027 A1 | 11/2009 | Glynn |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0168844 A1 | 7/2010 | Toomes et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0234940 A1 | 9/2010 | Dolan |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0054466 A1 | 3/2011 | Rothstein et al. |
| 2011/0098800 A1 | 4/2011 | Braido et al. |
| 2011/0098802 A1 | 4/2011 | Braido et al. |
| 2011/0137397 A1 | 6/2011 | Chau et al. |
| 2011/0172765 A1 | 7/2011 | Nguyen et al. |
| 2011/0208283 A1 | 8/2011 | Rust |
| 2011/0264206 A1 | 10/2011 | Tabor |
| 2011/0313510 A1* | 12/2011 | Gale ...................... A61L 31/18 623/1.15 |
| 2012/0022629 A1* | 1/2012 | Perera .................. A61F 2/24 623/1.11 |
| 2012/0035722 A1 | 2/2012 | Tuval |
| 2012/0078347 A1 | 3/2012 | Braido et al. |
| 2012/0078352 A1 | 3/2012 | Wang et al. |
| 2012/0101572 A1 | 4/2012 | Kovalsky et al. |
| 2012/0123529 A1 | 5/2012 | Levi et al. |
| 2012/0303116 A1 | 11/2012 | Gorman, III et al. |
| 2013/0274873 A1 | 10/2013 | Delaloye et al. |
| 2014/0121763 A1 | 5/2014 | Duffy et al. |
| 2014/0155997 A1 | 6/2014 | Braido |
| 2014/0214153 A1 | 7/2014 | Ottma et al. |
| 2014/0214159 A1 | 7/2014 | Vidlund et al. |
| 2014/0228946 A1 | 8/2014 | Chau et al. |
| 2014/0303719 A1 | 10/2014 | Cox et al. |
| 2014/0324164 A1 | 10/2014 | Gross et al. |
| 2014/0343671 A1 | 11/2014 | Yohanan et al. |
| 2014/0350668 A1 | 11/2014 | Delaloye et al. |
| 2014/0350669 A1 | 11/2014 | Gillespie et al. |
| 2015/0073545 A1* | 3/2015 | Braido ................. A61F 2/2412 623/2.18 |
| 2015/0209136 A1* | 7/2015 | Braido ................. A61F 2/2403 623/2.18 |
| 2016/0024699 A1* | 1/2016 | Aldridge ............... D01F 1/106 442/337 |
| 2016/0249935 A1* | 9/2016 | Hewitt ............. A61B 17/12031 606/200 |
| 2018/0071089 A1 | 3/2018 | Kaleta et al. |
| 2018/0133003 A1* | 5/2018 | Levi ..................... A61F 2/2418 |

FOREIGN PATENT DOCUMENTS

| | | |
|---|---|---|
| DE | 10121210 B4 | 11/2005 |
| DE | 102005003632 A1 | 8/2006 |
| DE | 202008009610 U1 | 12/2008 |
| EP | 0850607 A1 | 7/1998 |
| EP | 1000590 A1 | 5/2000 |
| EP | 1584306 A1 | 10/2005 |
| EP | 1598031 A2 | 11/2005 |
| EP | 1360942 B1 | 12/2005 |
| EP | 1926455 A2 | 6/2008 |
| EP | 2537487 B1 | 12/2012 |
| FR | 2850008 A1 | 7/2004 |
| FR | 2847800 B1 | 10/2005 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 01028459 A1 | 4/2001 |
| WO | 0149213 A2 | 7/2001 |
| WO | 01054625 A1 | 8/2001 |
| WO | 01056500 A2 | 8/2001 |
| WO | 01076510 A2 | 10/2001 |
| WO | 0236048 A1 | 5/2002 |
| WO | 0247575 A2 | 6/2002 |
| WO | 02067782 A2 | 9/2002 |
| WO | 03047468 A1 | 6/2003 |

(56) References Cited

FOREIGN PATENT DOCUMENTS

| WO | 2005070343 A1 | 8/2005 |
|----|---------------|--------|
| WO | 06073626 A2 | 7/2006 |
| WO | 07071436 A2 | 6/2007 |
| WO | 08070797 A2 | 6/2008 |
| WO | 10008548 A2 | 1/2010 |
| WO | 10008549 A1 | 1/2010 |
| WO | 10096176 A1 | 8/2010 |
| WO | 10098857 A1 | 9/2010 |

OTHER PUBLICATIONS

Definition of "weave". Merriam-Webster Dictionary. https://www.merriam-webster.com/dictionary/weave. Apr. 2009. Retrieved Jan. 27, 2022.*

Andersen, et al., "Transluminal Implantation of Artificial Heart Valves. Description of a New Expandable Aortic Valve and Initial Results with Implantation by Catheter Technique in Closed Chest Pigs", European Heart Journal, vol. 13, No. 5, May 1992, pp. 704-708.

Andersen, Henning, "Transluminal Catheter Implanted Prosthetic Heart Valves", International Journal of Angiology, vol. 7, No. 2, Mar. 1998, pp. 102-106.

Braido, et al., Design U.S. Appl. No. 29/375,243, filed Sep. 20, 2010, titled "Surgical Stent Assembly".

Buellesfeld and Meier, "Treatment of Paravalvular Leaks Through Interventional Techniques", Multimedia Manual of Cardiothoracic Surgery: MMCTS, Jan. 2011, 8 pages.

De Cicco, et al., "Aortic Valve Periprosthetic Leakage: Anatomic Observations and Surgical Results", The Annals of Thoracic Surgery, vol. 79, No. 5, May 2005, pp. 1480-1485.

Dewey, et al., "Transapical Aortic Valve Implantation: An Animal Feasibility Study", The Annals of Thoracic Surgery, vol. 82, No. 1, Jul. 2006, pp. 110-116.

Gossel and Rihal, "Percutaneous Treatment of Aortic and Mitral Valve Paravalvular Regurgitation", Current Cardiology Reports, vol. 15, No. 8, Aug. 2013, 8 pages.

Heat Advisor, "Heart Repairs Without Surgery: Minimally Invasive Procedures Aim to Correct Valve Leakage", Technology Frontier, Sep. 2004, pp. 4-5.

Hijazi, et al., Textbook "Transcatheter Valve Repair", CRC Press, Jan. 2006, pp. 165-186.

Hourihan, et al., "Transcatheter Umbrella Closure of Valvular and Paravalvular Leaks", Journal of the American College of Cardiology, vol. 20, No. 6, Nov. 1992, pp. 1371-1377.

Huber, et al., "Direct-Access Valve Replacement: A Novel Approach for Off-Pump Valve Implantation Using Valved Stents", Journal of the American College of Cardiology, vol. 46, No. 2, Jul. 2005, pp. 366-370.

Knudsen, et al., "Catheter-Implanted Prosthetic Heart Valves: Transluminal Catheter Implantation of a New Expandable Artificial Heart Valve in the Descending Thoracic Aorta in Isolated Vessels and Closed Chest Pigs", The International Journal of Artificial Organs, vol. 16, No. 5, May 1993, pp. 253-262.

Lichtenstein, et al., "Transapical Transcatheter Aortic Valve Implantation in Humans: Initial Clinical Experience", Circulation, vol. 114, No. 6, Aug. 2006, pp. 591-596.

Lichtenstein, Samuel, "Closed Heart Surgery: Back to the Future", The Journal of Thoracic and Cardiovascular Surgery, vol. 131, No. 5, May 2006, pp. 941-943.

Mack, M.J., "Minimally Invasive Cardiac Surgery", Surgical Endoscopy and Other Interventional Techniques, vol. 20, No. 2, Apr. 2006, pp. S488-S492.

Moazami, et al., "Transluminal Aortic Valve Placement: A Feasibility Study with a Newly Designed Collapsible Aortic Valve", ASAIO Journal (American Society for Artificial Internal Organs), vol. 42, No. 5, 1996, pp. M381-M385.

Munoz, et al., "Guidance of Treatment of Perivalvular Prosthetic Leaks", Current Cardiology Reports, vol. 16, No. 1, Jan. 2014, 6 pages.

Quaden, et al., "Percutaneous Aortic Valve Replacement: Resection Before Implantation", European Journal of Cardio-Thoracic Surgery, vol. 27, No. 5, May 2005, pp. 836-840.

Rohde, et al., "Resection of Calcified Aortic Heart Leaflets in Vitro by Q-Switched 2 um Microsecond Laser Radiation", Journal of Cardiac Surgery, vol. 30, No. 2, Feb. 2015, pp. 157-162.

Ruiz, Carlos, "Overview of Pre-CE Mark Transcatheter Aortic Valve Technologies", Euro PCR, May 2010, 14 pages.

Swiatkiewicz, et al., "Percutaneous Closure of Mitral Perivalvular Leak", Kardiologia Polska, vol. 67, No. 7, 2009, pp. 762-764. (English Abstract Only).

Walther, et al., "Transapical Approach for Sutureless Stent-Fixed Aortic Valve Implantation: Experimental Results", European Journal of Cardio-Thoracic Surgery, vol. 29, No. 5, May 2006, pp. 703-708.

Webb, et al., "Percutaneous Aortic Valve Implantation Retrograde From the Femoral Artery", Circulation, vol. 113, No. 6, Feb. 2006, pp. 842-850.

Zegdi, et al., "Is It Reasonable to Treat All Calcified Stenotic Aortic Valves with a Valved Stent?: Results from a Human Anatomic Study in Adults", Journal of the American College of Cardiology, vol. 51, No. 5, Feb. 2008, pp. 579-584.

* cited by examiner

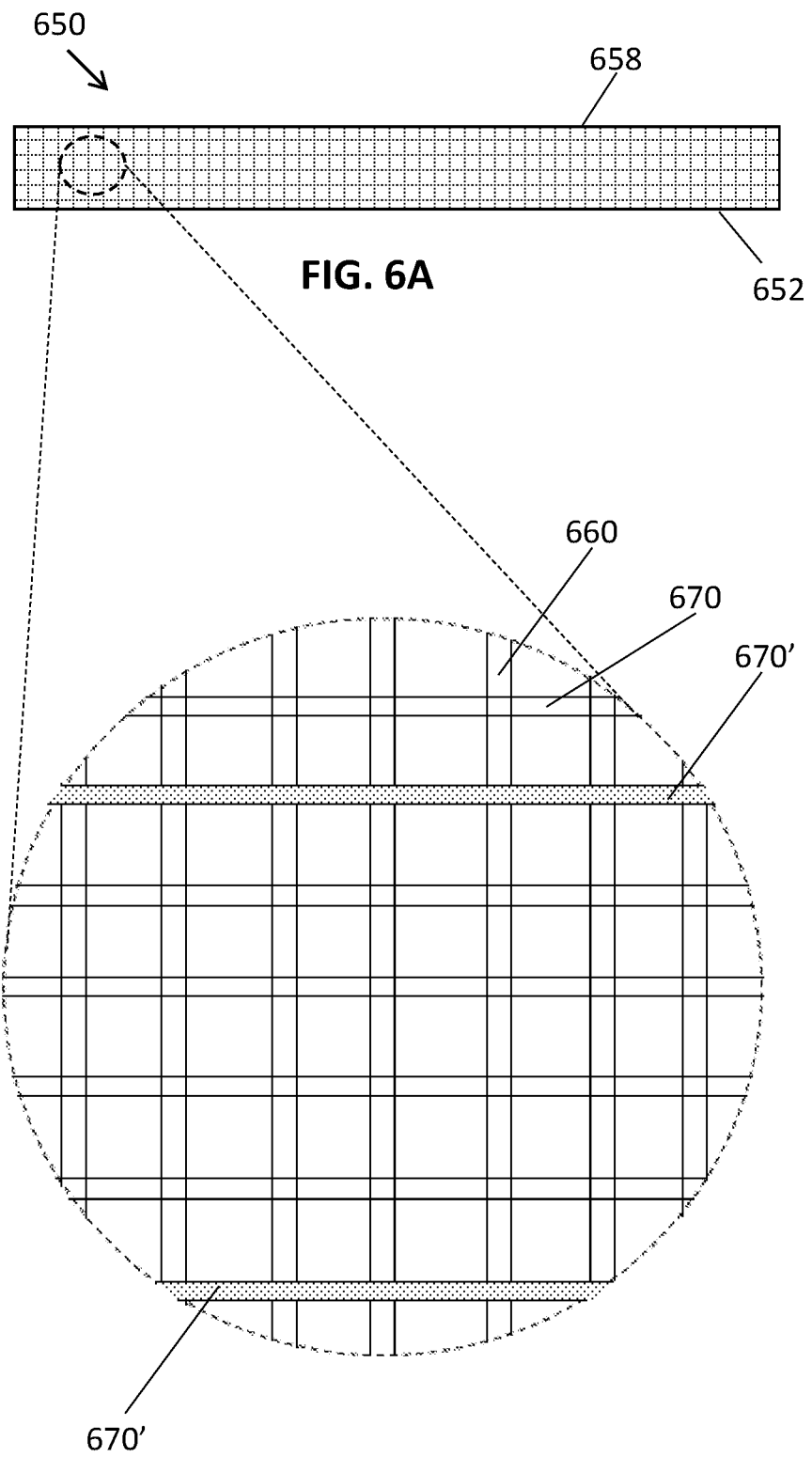

RADIOPAQUE OUTER CUFF FOR TRANSCATHETER VALVE

CROSS-REFERENCE TO RELATED APPLICATIONS

This application claims priority to the filing date of U.S. Provisional Patent Application No. 62/648,467 filed on Mar. 27, 2018, the disclosure of which is hereby incorporated by reference herein.

BACKGROUND OF THE DISCLOSURE

The present disclosure relates to heart valve replacement and, in particular, to collapsible prosthetic heart valves. More particularly, the present disclosure relates to collapsible prosthetic transcatheter heart valves that include radiopaque outer cuffs.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two common types of stents on which the valve structures are ordinarily mounted: a self-expanding stent and a balloon-expandable stent. To load such valves into a delivery apparatus and deliver them into a patient, the valve is first collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the valve, assuring its proper location, and then expanding a balloon positioned within the valve stent. For self-expanding valves, on the other hand, the stent automatically expands as a sheath covering the valve is withdrawn.

After implantation, imperfect sealing between the prosthetic valve and the native tissue at the site of implantation may cause complications such as paravalvular leakage ("PV leak") in which blood flows in a retrograde direction through one or more gaps formed between the structure of the implanted valve and cardiac tissue as a result of the imperfect sealing.

BRIEF SUMMARY

According to one embodiment of the disclosure, a prosthetic heart valve for replacing a native valve includes a stent having a plurality of struts, an inflow end, an outflow end, a collapsed condition and an expanded condition. A valve assembly may be disposed within the stent. A first cuff may be annularly disposed adjacent the stent. A second cuff may have a proximal end adjacent the inflow end of the stent and a distal end spaced apart from the proximal end. The second cuff may be annularly disposed about the stent radially outward of the first cuff and radially outward of the stent. The second cuff may be at least partly radiopaque.

Another embodiment of the disclosure includes a method of implanting a prosthetic heart valve into a native valve annulus of a patient. The method may include delivering the prosthetic heart valve to the native valve annulus while the prosthetic heart valve is maintained in a collapsed condition within a sheath of a delivery device. The prosthetic heart valve may include a stent having a plurality of struts, a first cuff, and a second cuff positioned radially outward of the first cuff and the stent. The method may include imaging the native valve annulus using fluoroscopy while the prosthetic heart valve is positioned adjacent the native valve annulus. A position of the second cuff may be determined relative to the native valve annulus using fluoroscopy. The prosthetic heart valve may be released from the delivery device and the prosthetic heart valve may be deployed into the native valve annulus.

BRIEF DESCRIPTION OF THE DRAWINGS

Various embodiments of the presently disclosed prosthetic heart valve may be more fully understood with reference to the following detailed description when read with the accompanying drawings.

FIG. 6A is a side view of an outer cuff in a flattened condition according to another embodiment of the disclosure.

FIG. 6B is an enlarged view of fibers forming the outer cuff of FIG. 6A.

DETAILED DESCRIPTION

As used herein in connection with a prosthetic heart valve, the term "inflow end" refers to the end of the heart valve through which blood enters when the valve is functioning as intended, and the term "outflow end" refers to the end of the heart valve through which blood exits when the valve is functioning as intended. As used herein, the term "proximal" refers to the inflow end of a prosthetic heart valve or to elements of a prosthetic heart valve that are relatively close to the inflow end, and the term "distal" refers to the outflow end of a prosthetic heart valve or to elements of a prosthetic heart valve that are relatively close to the outflow end. As used herein, the terms "generally," "substantially," and "about" are intended to mean that slight deviations from absolute are included within the scope of the term so modified Like numbers refer to similar or identical elements throughout. When used herein in the context of a prosthetic heart valve, or a component thereof, the lengthwise or axial direction refers to a direction parallel to a longitudinal axis passing through the center of the stent or heart valve from the inflow end to the outflow end. When used herein in the context of a prosthetic heart valve, or a component thereof, the circumferential direction refers to a direction extending along the circumference of the prosthetic heart valve.

Figure 1:
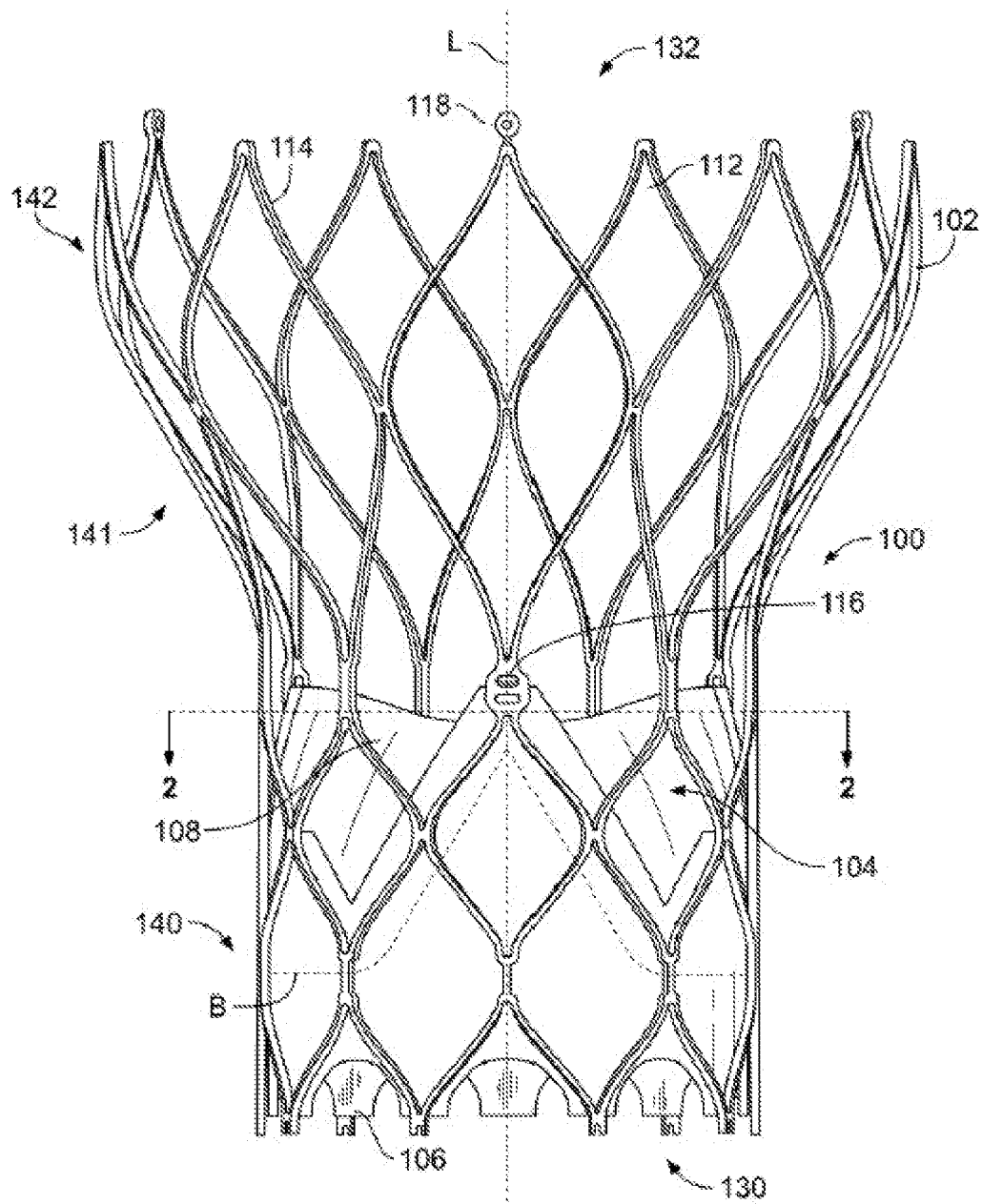
FIG. 1 is a front view of a collapsible prosthetic heart valve according to the prior art, shown in an expanded condition.

FIG. 1 shows a collapsible stent-supported prosthetic heart valve 100 according to the prior art, the prosthetic heart valve being shown in an expanded condition. Prosthetic heart valve 100 is designed to replace the function of the native aortic valve of a patient. Prosthetic heart valve 100 includes a stent 102 which serves as a frame for the valve elements. Stent 102 extends along a lengthwise or longitudinal axis L from an inflow or annulus end 130 to an outflow or aortic end 132, and includes an annulus section 140 adjacent inflow end 130 and an aortic section 142 adjacent outflow end 132. Annulus section 140 may be in the form of a cylinder having a substantially constant diameter along its length, and may have a relatively small transverse cross-section in the expanded condition in comparison to the transverse cross-section of aortic section 142. A transition section 141 may taper outwardly from annulus section 140 to aortic section 142. Each of the sections of stent 102 includes a plurality of cells 112 formed by interconnected struts 114. Each cell 112 may include four struts 114 connected together generally in a diamond shape so as to form a cell that may be readily collapsed and expanded. It will be appreciated that a smaller or larger number of struts may be used to form cells having a different shape. The cells 112 in each section of stent 102 may be connected to one another in one or more annular rows around the stent. For example, as shown in FIG. 1, annulus section 140 may have two annular rows of complete cells 112, with the cells in one annular row offset by one-half cell width in the circumferential direction from the cells in the other annular row. Aortic section 142 and transition section 141 may each have one or more annular rows of complete or partial cells 112. The cells in aortic section 142 may be larger than the cells in annulus section 140 so as to better enable prosthetic valve 100 to be positioned within the aortic annulus without the structure of stent 102 interfering with blood flow to the coronary arteries. At least partly due to the shape of cells 112, stent 102 elongates in the direction of longitudinal axis L as the cells collapse when the stent transitions from the expanded condition to the collapsed condition, and shortens in the direction of longitudinal axis L as the stent transitions from the collapsed condition to the expanded condition.

Stent 102 may include one or more retaining elements 118 at outflow end 132, the retaining elements being sized and shaped to cooperate with retaining structures provided on a deployment device (not shown). The engagement of retaining elements 118 with the retaining structures on the deployment device may help maintain prosthetic heart valve 100 in assembled relationship with the deployment device, minimize longitudinal movement of the prosthetic heart valve relative to the deployment device during unsheathing or resheathing procedures, and help prevent rotation of the prosthetic heart valve relative to the deployment device as the deployment device is advanced to the target location and during deployment. One such deployment device is described in U.S. Patent Publication No. 2012/0078352, the entire contents of which are hereby incorporated by reference herein.

Stent 102 may also include a plurality of commissure attachment features 116 for mounting the commissures of the valve assembly to the stent. As can be seen in FIG. 1, each commissure attachment feature 116 may lie at the intersection of four cells 112, two of the cells being adjacent one another in the same annular row, and the other two cells being in different annular rows and lying in end-to-end relationship. Commissure attachment features 116 may be positioned entirely within annulus section 140 or at the juncture of annulus section 140 and transition section 141, and may include one or more eyelets or apertures which facilitate the suturing of the leaflet commissures to stent 102. Stent 102 may be formed as a unitary structure, for example, by laser cutting or etching a tube of a superelastic and/or shape-memory metal alloy, such as a nickel-titanium alloy of the type sold under the designation nitinol. Such a unitary structure may be referred to as a "non-woven" structure in that it is not formed by weaving or winding one or more filaments. Although the stent 102 described herein is part of a self-expanding prosthetic heart valve, it will be appreciated that the concepts and features described herein may also be applied to a prosthetic heart valve that is balloon-expandable.

Prosthetic heart valve 100 includes a valve assembly 104 positioned in the annulus section 140 of stent 102. Valve assembly 104 includes a plurality of leaflets 108 that collectively function as a one way valve by coapting with one another, and a cuff 106 positioned on the luminal surface of stent 102 surrounding leaflets 108. As prosthetic heart valve 100 is intended to replace the aortic valve (which ordinarily is a tri-leaflet valve), it is shown in FIG. 1 with three leaflets 108. Adjacent leaflets 108 join one another at leaflet commissures. Each of the leaflet commissures may be sutured to a respective one of the three commissure attachment features 116. Between the leaflet commissures, each leaflet 108 may be sutured to stent 102 and/or to cuff 106 along a leaflet belly B, indicated with broken lines in FIG. 1. Leaflets 108 may be joined to stent 102 and/or to cuff 106 by techniques known in the art other than suturing. Above belly B, leaflets 108 are free to move radially inward to coapt with one another along their free edges. When prosthetic heart valve 100 is implanted in the native aortic valve annulus, blood flows in an antegrade direction from inflow end 130, past leaflets 108, and toward outflow end 132. This occurs when the pressure in the left ventricle is greater than the pressure in the aorta, forcing leaflets 108 to open. When the pressure in the aorta is greater than the pressure in the left ventricle, leaflets 108 are forced closed and coapt with one another along their free edges, blocking blood from flowing through prosthetic heart valve 100 in a retrograde direction from outflow end 132 to inflow end 130. It will be appreciated that prosthetic heart valves according to aspects of the present disclosure may have more or less than the three leaflets 108 and commissure attachment features 116 shown in FIG. 1 and described above.

Although cuff 106 is shown in FIG. 1 as being disposed on the luminal or inner surface of annulus section 140, the cuff may be disposed on the abluminal or outer surface of the annulus section, or may cover all or part of either or both of the luminal and abluminal surfaces of the annulus section. Cuff 106 may be scalloped at the inflow end 130 of stent 102, and may have a zig-zag structure at its outflow end, following certain stent struts 114 up to commissure attachment features 116 and other stent struts closer to the inflow end of the stent at circumferential positions between the commissure attachment features. As is shown in FIG. 1, in one example, the entirety of valve assembly 104, including the leaflet commissures, is positioned in the annulus section 140 of stent 102. When open, leaflets 108 may remain substantially completely within annulus section 140, or they may be designed to extend into transition section 141. In the embodiment shown, substantially the entirety of valve assembly 104 is positioned between the inflow end 130 of stent 102 and commissure attachment features 116, and none of the valve assembly is positioned between the commissure attachment features and the outflow end 132 of the stent.

In operation, prosthetic heart valve 100 described above may be used to replace a native heart valve, such as the aortic valve; a surgical heart valve; or a heart valve that has undergone a surgical procedure. Prosthetic heart valve 100 may be delivered to the desired site (e.g., near the native aortic annulus) using any suitable delivery device. During delivery, prosthetic heart valve 100 is disposed inside the delivery device in the collapsed condition. The delivery device may be introduced into the patient using any known percutaneous procedure, such as a transfemoral, transapical, or transseptal delivery procedure. Once the delivery device has reached the target site, the user may deploy prosthetic heart valve 100. Upon deployment, prosthetic heart valve 100 expands into secure engagement within the native aortic annulus. When prosthetic heart valve 100 is properly positioned inside the heart, it works as a one-way valve, allowing blood to flow in one direction and preventing blood from flowing in the opposite direction.

Figure 2:
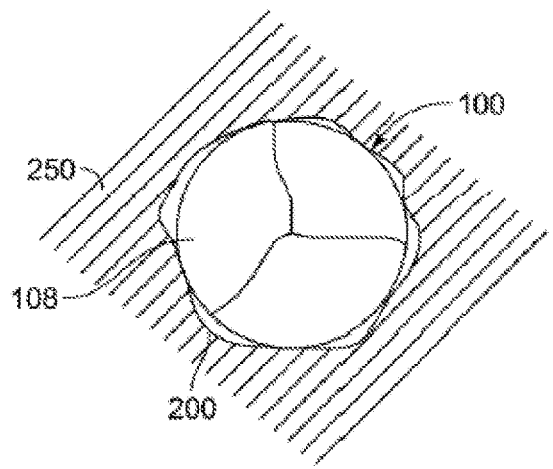
FIG. 2 is a highly schematic transverse cross-sectional view of the prior art prosthetic heart valve implanted in a patient, taken along line 2-2 of FIG. 1.

FIG. 2 is a highly schematic transverse cross-sectional illustration taken along line 2-2 of FIG. 2 and showing prosthetic heart valve 100 with leaflets 108 disposed within native valve annulus 250. As can be seen, the substantially circular annulus section 140 of stent 102 is disposed within a non-circular native valve annulus 250. At certain locations around the perimeter of prosthetic heart valve 100, gaps 200 are formed between the heart valve and native valve annulus 250. Retrograde blood flow through these gaps and around the outside of the valve assembly 104 of prosthetic heart valve 100 can result in PV leak or regurgitation and other inefficiencies which can reduce cardiac performance. Such improper fitment may be due to suboptimal native valve annulus geometry, for example, as a result of calcification of the tissue of native valve annulus 250 or the presence of unresected native leaflets.

Figure 3B:
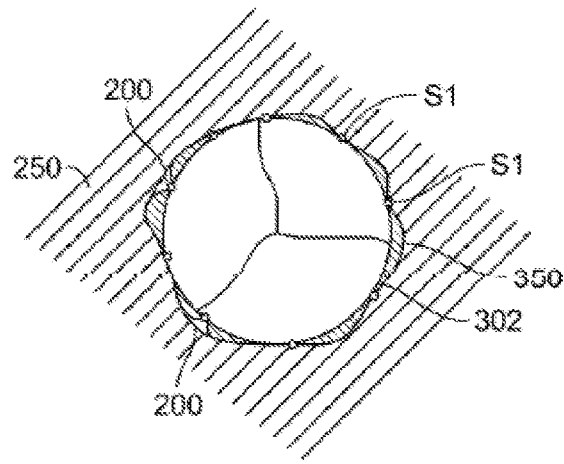
FIG. 3B is a highly schematic transverse cross-sectional view of a prosthetic heart valve including the stent and cuff of FIG. 3A implanted in a patient.
Figure 3A:
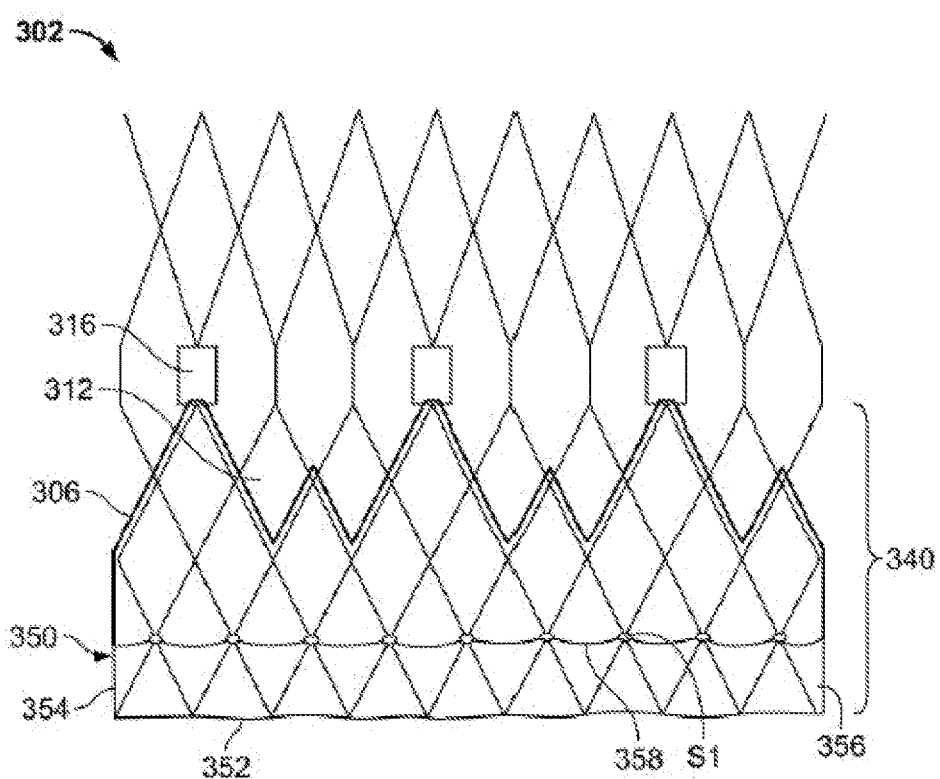
FIG. 3A is a schematic developed view of a stent with an outer cuff in an expanded condition according to an embodiment of the disclosure.

FIG. 3A illustrates the stent 302 of a prosthetic heart valve according to an aspect of the disclosure. Stent 302 may be used in a prosthetic heart valve that is similar or identical to prosthetic heart valve 100 described above, with certain exceptions. For example, the annulus section 340 of stent 302 may include three rows of cells 312 instead of two rows, although in some embodiments stent 302 may include only two rows of cells in the annulus section. Although commissure attachment features 316 of stent 302 are illustrated schematically as open rectangles in FIG. 3A, the commissure attachment features may have a form similar to commissure attachment features 116 shown in FIG. 1, or any other suitable form having any number of rows or columns of eyelets and/or eyelets of different sizes and/or shapes positioned in any arrangement on the commissure attachment feature. A cuff 306 similar or identical to cuff 106 may be positioned on the luminal or internal surface of stent 302. Rather than a scalloped inflow end as with cuff 106, however, cuff 306 may have a straight inflow end. In order to help minimize or eliminate PV leak, for example through the gaps 200 shown in FIG. 2, additional material may be coupled to the exterior of stent 302 as an outer cuff 350. In the illustrated example, outer cuff 350 may have a substantially rectangular shape and may be wrapped around the circumference of stent 302 at the inflow end of the stent so as to overlap in the longitudinal direction of the stent with cuff 306. Outer cuff 350 may be a single piece of material having a proximal edge 352, two side edges 354, 356, and a distal edge 358. Preferably, the proximal edge 352 of outer cuff 350 is coupled to stent 302 and/or to inner cuff 306 at or near the inflow end of the stent, for example by a continuous line of sutures (not shown), with the side edges 354 and 356 of the outer cuff joined to one another so that retrograde blood flow entering the space between the outer cuff and the inner cuff cannot pass in the retrograde direction beyond the combined cuffs. In order to allow retrograde blood flow to enter the space between outer cuff 350 and inner cuff 306, the distal edge 358 of the outer cuff may be attached to stent 302 and/or to inner cuff 306 at locations that are spaced apart in the circumferential direction. The distal edge 358 of outer cuff 350 may, for example, be sutured to stent 302 and/or to inner cuff 306 at attachment points S1 located where each cell 312 in the proximalmost row of cells intersects with an adjacent cell in that same row. In the illustrated example, since there are nine cells 312 in the proximalmost row, there are nine separate attachment points S1 at which the distal edge 358 of outer cuff 350 may be sutured or otherwise attached to stent 302 and/or inner cuff 306. Retrograde blood flow around the abluminal surface of stent 302 may enter the pocket or space between outer cuff 350 and inner cuff 306 via the spaces between adjacent attachment points S1. Once retrograde blood flow enters this space, outer cuff 350 may tend to billow outwardly, helping to fill any of gaps 200 between the prosthetic heart valve and native valve annulus 250. Although the foregoing description uses the term "inner" in connection with cuff 306, that is merely intended to indicate that cuff 306 is positioned radially inward of outer cuff 350. Inner cuff 306 may be located either on the luminal or abluminal side of stent 302, or on both sides.

Although described as a single piece of material above, outer cuff 350 may comprise multiple pieces of material that, when joined together, form a similar shape and provide similar function as described above for the outer cuff. Also, rather than being formed of a single substantially rectangular piece of material that is wrapped around the circumference of stent 302, outer cuff 350 may be formed as a continuous annular web without side edges 354, 356. Preferably, outer cuff 350 has an axial height measured from its proximal edge 352 to its distal edge 358 that is approximately half the axial height of a cell 312 in the proximalmost row of cells in stent 302 as measured along the major axis of the cell between two of its apices when the cell is in an expanded condition. However, outer cuff 350 may have other suitable heights, such as the full axial height of a cell 312 in the proximalmost row of cells, or more or less than the full axial height of a cell 312 in the proximalmost row of cells. Still further, although inner cuff 306 and outer cuff 350 are described above as separate pieces of material joined to stent 302 and to each other, the cuffs may be formed integrally with one another from a single piece of material that is wrapped around the proximal edge of the stent, with the distal edge 358 of the outer portion of the cuff joined to the stent and/or to the inner portion of the cuff at attachment points S1 as described above. With this configuration, the proximal edge 352 of outer cuff 350 does not need to be sutured to stent 302, although it still may be preferable to provide such attachment. Inner cuff 306 and outer cuff 350 may be formed of the same or different materials, including any suitable biological material or polymer such as, for example, polyethylene terephthalate (PET), polytetrafluoroethylene (PTFE), ultra-high molecular weight polyethylene (UHMWPE), polyurethane, polyvinyl alcohol, silicone, or combinations thereof.

Figure 4A:
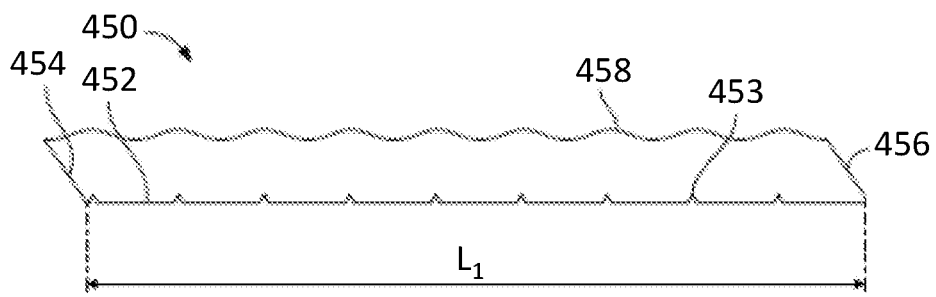
FIG. 4A is a side view of an outer cuff with notches in a flattened condition according to another embodiment of the disclosure.

FIG. 4A illustrates an outer cuff 450 that may be used, instead of outer cuff 350, with an inner cuff 306 and a stent similar or identical to stent 302. Outer cuff 450 generally has a straight inflow or proximal edge 452, correspondingly angled side edges 454 and 456, and a scalloped outflow or distal edge 458, and may be formed from any of the materials noted above for forming the other cuffs described herein, either from a single piece of material, from more than one piece of material, or as a single tubular member (i.e., without side edges 454 and 456). Outer cuff 450 may be wrapped around stent 302 with edges 454 and 456 sutured or otherwise attached to one another. The proximal edge 452 of outer cuff 450 may be attached to the inflow end of stent 302 and/or to inner cuff 306, for example by a continuous line of sutures. Alternatively, the proximal edge 452 of outer cuff 450 may be attached to inner cuff 306 so that the outer cuff 450 is positioned at any height between the proximal and distal edges of the inner cuff 306. It should also be understood that although other cuffs herein are shown with a straight distal edge, those cuffs may have a scalloped distal edge as shown in FIG. 4A, or outer cuff 450 may have a substantially straight distal edge. Preferably, the attachment points coupling outer cuff 450 to stent 302 and/or inner cuff 306 are positioned at the peaks of distal edge 458, with the troughs not being directly coupled to the stent or the inner cuff.

Figure 4B:
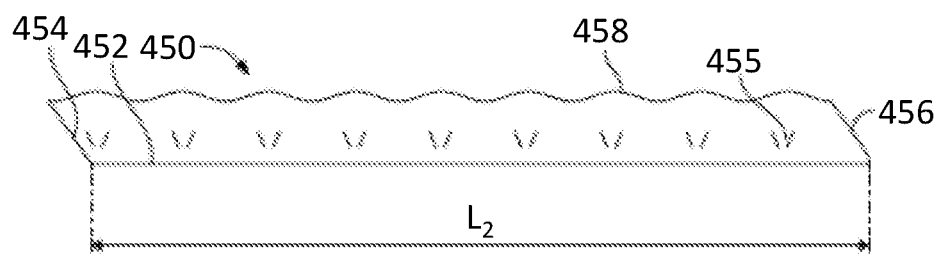
FIG. 4B is a side view of the outer cuff of FIG. 4A after connecting portions of the outer cuff adjacent the notches.

Prior to attachment to stent 302 and/or inner cuff 306, the substantially straight proximal edge 452 of outer cuff 450 may be interrupted by a plurality of spaced notches 453. Each notch 453 may be substantially triangular in shape with the base of the triangle (i.e., the base of the notch) positioned along proximal edge 452. The proximal edge 452 of outer cuff 450 has an end-to-end length $L_1$ such that, if outer cuff 450 is wrapped into a tube so that edges 454 and 456 mate, the circumference of the proximal edge will have a greater length than the circumference of the stent 302 (in an expanded condition) at the position at which outer cuff 450 is intended to connect to the stent or inner cuff. Prior to attachment to stent 302, the notches 453 may be closed by coupling the portions of proximal edge 452 adjacent each notch 453 to one another, for example by sutures, adhesives, or any other suitable method, so that the proximal edge 452 is substantially continuous without interruption, as shown in FIG. 4B. Because the portions of proximal edge 452 adjacent each notch 453 are pulled together and coupled to one another, the length $L_2$ of the proximal edge 452 is reduced compared to the length $L_1$. The reduction in the length of the proximal edge 452 upon closing the notches 453 is substantially equal to the aggregate length of the open bases of the notches. The length of the open base of each notch 453 may be selected depending on, for example, the number of cells in the stent 302 and the size of the prosthetic heart valve incorporating the stent and the outer cuff 450. In the case of a 32 mm size valve having nine cells 312 in the proximalmost row, the base of each notch 453 may be between about 0.04 inches (about 1.0 mm) and about 0.06 inches (about 1.5 mm) long, preferably about 0.05 inches (about 1.27 mm) long. Preferably, once the open bases of notches 453 are closed, the resulting length $L_2$ of proximal edge 452 is substantially equal to the circumference of the portion of stent 302 (in an expanded condition) or the portion of inner cuff 306 to which the outer cuff 450 will be attached. Because the length of proximal edge 452 decreases upon coupling together the portions of the proximal edge adjacent each notch 453, the material of outer cuff 450 may gather at the positions of the notches 453 to form puckered areas 455, as shown in FIG. 4B. In the illustrated embodiment, outer cuff 450 includes nine notches 453, or in other words one notch for each cell 312 in the proximalmost row, although such a one-to-one correspondence is not always required.

Figure 4C:
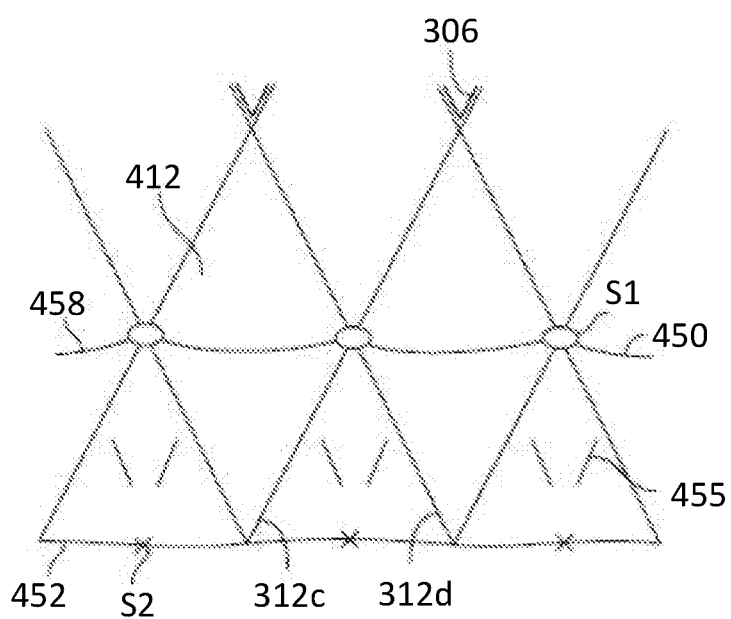
FIG. 4C is a highly schematic view of the outer cuff of FIG. 4B coupled to a stent and/or inner cuff such as that shown in FIG. 3A.

As shown in FIG. 4C, the distal edge 458 of outer cuff 450 may be attached to stent 302 and/or inner cuff 306, for example on the abluminal surface of the stent along the proximalmost row of cells 312, at attachment points S1, similar to the attachment of outer cuff 350 to stent 302 and/or inner cuff 306 as described in connection with FIG. 3A. In particular, each peak of distal edge 458 may be attached to stent 302 and/or inner cuff 306 at the locations at which two adjacent cells 312 in the proximalmost row of cells intersect one another, with the portions of the distal edge between attachment points S1 remaining detached from both the stent and the inner cuff. As shown in FIG. 4A, the notches 453 are preferably positioned so they are substantially aligned in the axial direction with the peaks of the distal edge 458 of outer cuff 450. With this configuration, once the outer cuff 450 is coupled to stent 302 and/or inner cuff 306, the puckered portions 455 of the outer cuff are positioned between strut 312c of one cell and strut 312d of a circumferentially adjacent cell in the proximalmost row of cells. The puckered portions 455 of outer cuff 450 reduce the tautness of, or increase the slack in, outer cuff 450 at these positions, allowing for blood located between the outer cuff and inner cuff 306 to more easily migrate into those locations. In particular, retrograde blood flowing into the space between outer cuff 450 and inner cuff 306 may more easily migrate across struts 312c and 312d due to the additional space provided by the puckered portions 455 of the outer cuff which, in turn, allows for the outer cuff to billow outwardly into gaps 200 more completely.

As shown in FIG. 4C, the open bases of notches 453 may be closed with a suture at attachment points S2 prior to coupling the outer cuff 450 to the stent 302 and/or inner cuff 306. The sutures at attachment points S2 may be separate from a substantially continuous suture line coupling the proximal edge 452 of outer cuff 450 to the stent 302 and/or inner cuff 306. However, other methods may be used to couple the proximal edge 452 of outer cuff 450 to the stent 302 and/or inner cuff 306. In one example, the open bases of notches 453 are not closed in a step that is separate from attaching the proximal edge 452 of the outer cuff 450 to the stent 302 and/or inner cuff 306. For example, the proximal edge 452 of outer cuff 450 may be attached to the stent 302 and/or inner cuff 306 by a single continuous suture line, without providing separate sutures to close the open bases of the notches 453. In such a configuration, a suture is used to couple the proximal edge 452 of outer cuff 450 to the stent 302 and/or inner cuff 306, and as the suture approaches a notch 453, the user may gather portions of the proximal edge to close the open base of the notch 453 and continue the suturing so that an additional suture element is not needed to hold the notches 453 in the closed condition. It should be understood that once the portions of the proximal edge 452 of outer cuff 450 adjacent each notch 453 are coupled together, it may not be critical to ensure that the entire space of the notch 453 is completely sealed. For example, because the notches 453 are small and the cycling between systole and diastole is fast, small gaps may remain in outer cuff 450 where the notches 453 are positioned without significant leakage of blood through those gaps. Allowing some amount of gap to remain in notches 453 may even be beneficial. For example, leaving such gaps may provide openings for a user to eliminate air bubbles trapped between outer cuff 450 and inner cuff 306 prior to implanting the prosthetic valve into the patient.

In the embodiment of outer cuff 450 shown in FIGS. 4A-C, the outer cuff includes nine peaks and nine troughs, with nine notches 453 axially aligned with corresponding peaks, and stent 302 includes nine cells 312 in the proximalmost row of cells. Although it may be desirable to have this correspondence between peaks, notches 453, and cells 312, such correspondence is not necessary. For example, the outer cuff 450 may include more or fewer notches 453 than the number of peaks and troughs, and the number of notches does not need to match the number of cells 312 in the row of cells positioned adjacent the outer cuff. If a relatively large total distance is cut out from the proximal edge 452 of outer cuff 450 by notches 453, a relatively large amount of material of the outer cuff will become puckered, creating additional channels for blood to flow across struts 312c and 312d. However, if too much of the fabric of outer cuff 450 is puckered, the resulting prosthetic heart valve may require greater forces to collapse and load into a delivery device and may even require a larger size delivery device.

Still further, although notches 453 are shown as triangular in shape, other shapes may be suitable. For example, rectangular or trapezoidal shapes may be suitable for the notches 453. However, triangular shapes may help produce a substantially continuous proximal edge 452 as the bases of notches 453 are closed, while at the same time minimizing the size of any gaps that may be formed and through which blood may escape from between outer cuff 450 and inner cuff 306. The size of the notches may also be varied to alter the characteristics of the resulting puckered portions 455. For example, a smaller notch would result in a smaller puckered portion compared to a larger notch. A greater number of smaller notches could therefore result in many smaller puckered portions, while a smaller number of larger notches would result in a fewer larger puckered portions.

When implanting a prosthetic heart valve similar to prosthetic heart valve 100 that includes an outer cuff similar to outer cuff 350 or 450, it may be preferable to ensure that the outer cuff is positioned appropriately within native valve annulus 250 to help reduce or prevent PV leak. Typically, because transcatheter prosthetic heart valves such as prosthetic heart valve 100 are delivered and implanted without direct visualization, imaging techniques such as fluoroscopy are used during delivery and/or deployment of the prosthetic valve in order to help confirm proper placement of the prosthetic valve within native valve annulus 250. Fluoroscopy relies at least partially on a material being visible under x-ray imaging—a property known as radiodensity or radiopacity. Metals and metal alloys, such as nitinol, are typically readily visible under x-ray imaging. Thus, during a traditional procedure for delivery and deployment of prosthetic heart valve 100, confirmation of satisfactory positioning of the prosthetic heart valve is based in large part on the confirmation of the positioning of stent 102, since the stent is readily visible under fluoroscopic imaging. However, other components of prosthetic heart valve 100 may be difficult or impossible to view under traditional fluoroscopic imaging because those components are radiolucent. Inner cuff 306, for example, is typically formed of a radiolucent material. If an outer cuff, such as outer cuff 350 or 450, is similarly formed of a radiolucent material, it may be difficult or impossible to directly confirm via fluoroscopy if the outer cuff is positioned correctly within native valve annulus 250 to maximize the prevention of PV leak.

Figure 5A:
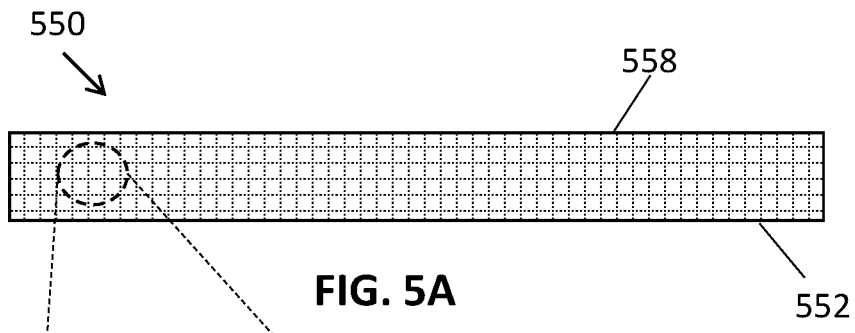
FIG. 5A is a side view of an outer cuff in a flattened condition according to another embodiment of the disclosure.

FIG. 5A illustrates an outer cuff 550 for use with a prosthetic heart valve. In FIG. 5A, outer cuff 550 is shown as a rectangular sheet. The features of outer cuff 550 described below focus on materials that form the outer cuff, and it should be understood that the particular shape or configuration of the outer cuff may be similar or identical to outer cuff 450, outer cuff 350, or any other suitable outer cuff, including those described in U.S. patent application Ser. No. 15/702,942, the disclosure of which is hereby incorporated by reference herein. In addition, although outer cuffs 350 and 450 are described as being formed of particular materials, it should be understood that the material properties described in connection with outer cuff 550 may be implemented in outer cuffs 350 and 450.

Figure 5B:
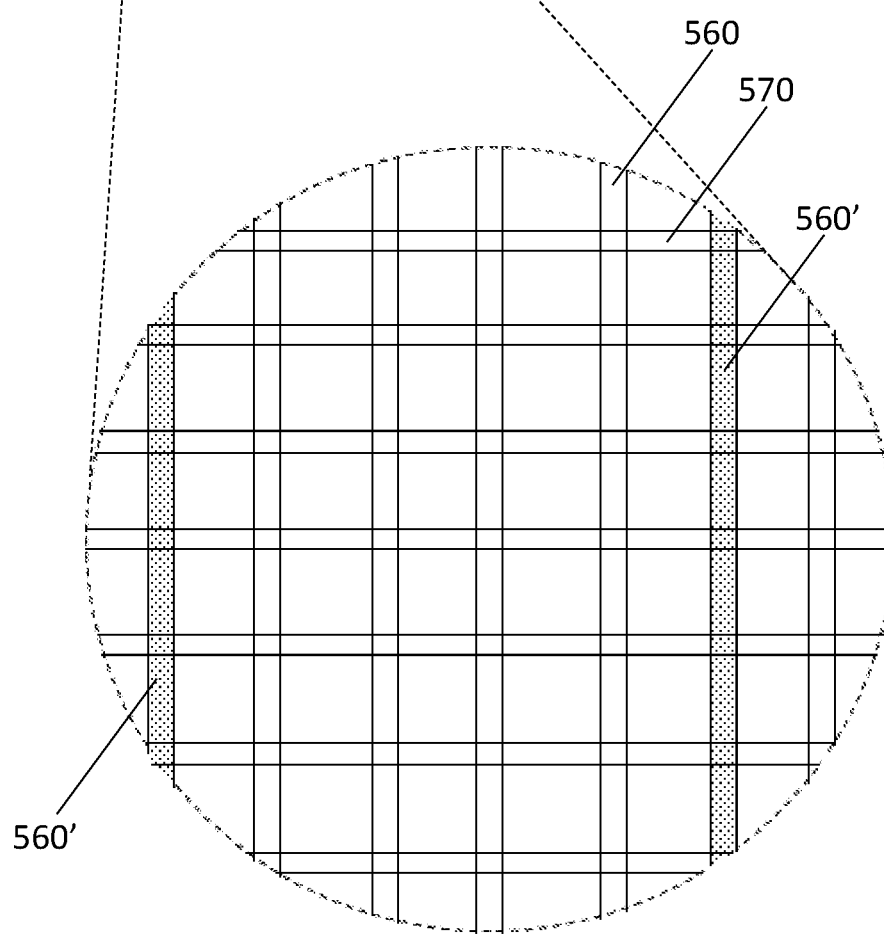
FIG. 5B is an enlarged view of fibers forming the outer cuff of FIG. 5A.

Outer cuff 550 may be formed of a fabric, with the fabric being formed of one or more fibers that are woven together. FIG. 5B illustrates that the fabric forming outer cuff 550 may be formed by a plurality of first fibers 560 extending in a first fiber direction interwoven with a plurality of second fibers 570 extending in a second fiber direction transverse to the first fiber direction. In the illustrated embodiment, first fibers 560 are substantially orthogonal to second fibers 570, with the second fibers extending substantially parallel to the proximal edge 552 and the distal edge 558 of outer cuff 550 (and/or substantially orthogonal to a central longitudinal axis of a prosthetic heart valve incorporating outer cuff 550), and the first fibers extending substantially orthogonal to the proximal and distal edges of the outer cuff (and/or substantially parallel to a central longitudinal axis of a prosthetic heart valve incorporating outer cuff 550). However, it should be understood that first fibers 560 and second fibers 570 may extend in other directions than shown. For example, first fibers 560 and second fibers 570 may both extend at angles of about 45 degrees with respect to the proximal edge 552 and the distal edge 558 of outer cuff 550 (and/or at angles of about 45 degrees or other oblique angles with respect to a central longitudinal axis of a prosthetic heart valve incorporating outer cuff 550), with the first fibers being substantially orthogonal to the second fibers.

First fibers 560 and second fibers 570 may be formed of a radiolucent material, such as PET, PTFE, UHMWPE, or combinations thereof. However, selected ones of the first fibers may be formed of a radiopaque material, represented in the figures with stippling and with an apostrophe symbol added to the reference number. Thus, in the illustrated embodiment, selected first fibers 560' are formed of a radiopaque material. All of the second fibers 570 may be radiolucent, whereas radiopaque first fibers 560' are interposed between groups of adjacent radiolucent first fibers 560. In one example, groups of four adjacent or consecutive radiolucent first fibers 560 are separated by individual radiopaque first fibers 560'. Radiopaque fibers 560' may be formed by any suitable process. For example, a monofilament of desired material may be impregnated with one or more radiopacifiers such as barium sulfate ($BaSO_4$) and/or bismuth trioxide ($Bi_2O_3$). However, it should be understood that any of the fibers of outer cuff 550 may be monofilaments or otherwise may be woven multi-ply fibers. For example, radiopaque fibers 560' may be multi-ply fibers in which all or fewer than all of the individual plies of the multi-ply fiber are radiopaque.

It may be desirable for outer cuff 550 to have radiopacity such that, under fluoroscopic visualization during an implantation procedure, the outer cuff is readily visible to a physician, while the radiopacity of the outer cuff does not interfere or significantly interfere with the ability to visualize portions of the struts of stent 302 positioned radially inward of the outer cuff. In order to achieve the ability to readily visualize both outer cuff 550 and portions of underlying stent 302 during fluoroscopic visualization, it is preferable that radiopaque fibers 560' with relatively high radiopacity are spaced relatively far from one another, or otherwise that radiopaque fibers that are spaced relatively close to one another have relatively low radiopacity. In other words, when the spacing between adjacent radiopaque fibers 560' is large, the radiopaque fibers may be highly radiopaque, as the overall radiopacity of outer cuff 550 may be less than the radiopacity of stent 302 due to the large spacing of adjacent radiopaque fibers. On the other hand, if the spacing between adjacent radiopaque fibers 560' is small, the radiopaque fibers preferably are less radiopaque than in the example given directly above. As used herein, the phrases "more radiopaque" or "less radiopaque" are intended to denote a quantitative difference in radiopacity, e.g. in the relative amount of x-ray photons that an item inhibits from passing through the item under similar or identical imaging conditions. Radiopacity may be measured by any generally accepted methodology known in the art, such as via the Hounsfield scale or the ASTM F640 Standard Test Methods for Determining Radiopacity for Medical Use. Thus, in the example of FIG. 5B, while individual radiopaque fibers 560' may have a high level of radiopacity (e.g. similar radiopacity to struts of stent 302, or less radiopacity than the struts), the overall radiopacity of outer cuff 550 under fluoroscopic imaging may still allow the struts of the portions of the stent underlying the outer cuff to be readily visualized.

It should be understood that the term "fiber" is not intended to impart any special structure on first fibers 560, radiopaque fibers 560', or second fibers 570. In other words, first fibers 560 may be filaments (monofilaments or multi-ply filaments), yarns (single ply or multi-ply), or combinations thereof. Further, first fibers 560 may each be a single fiber. Alternatively, all first fibers 560 may be formed of a single continuous fiber that wraps or turns upon itself to form the pattern shown in FIG. 5B. Still further, any combination of individual and continuous fibers may be used to form first fibers 560. This also applies to radiopaque fibers 560' and second fibers 570.

Although particular examples of radiopaque fibers 560' are provided above, it should be understood that other materials and constructions may be suitable for forming the radiopaque fibers. For example, U.S. Pat. No. 9,687,593, the disclosure of which is hereby incorporated by reference herein, discloses various examples of the creation of radiopaque fibers that may be suitable for use in outer cuff 550.

FIGS. 6A-6B illustrate an outer cuff 650 having a proximal edge 652 and a distal edge 658, the outer cuff being in the form of a fabric comprising first fibers 660 and second fibers 670. Outer cuff 650 may be identical to outer cuff 550 described above, with the exception that, instead of having radiopaque first fibers 560', the fabric of outer cuff 650 includes radiolucent first fibers 660, with selected ones of the second fibers 670 being radiopaque fibers 670'. As illustrated in FIG. 6B, groups of four adjacent or consecutive second fibers 670 may be interrupted by a single radiopaque fiber 670'. The variations described above in connection with outer cuff 550 may similarly apply to outer cuff 650. For example, the spacing between adjacent radiopaque second fibers 670' may be smaller than shown, preferably with the individual radiopaque fibers having a relatively small amount of radiopacity, or the spacing between adjacent radiopaque second fibers may be greater than shown, preferably with the individual radiopaque fibers having a relatively large amount of radiopacity.

Figures 7A, 7B:
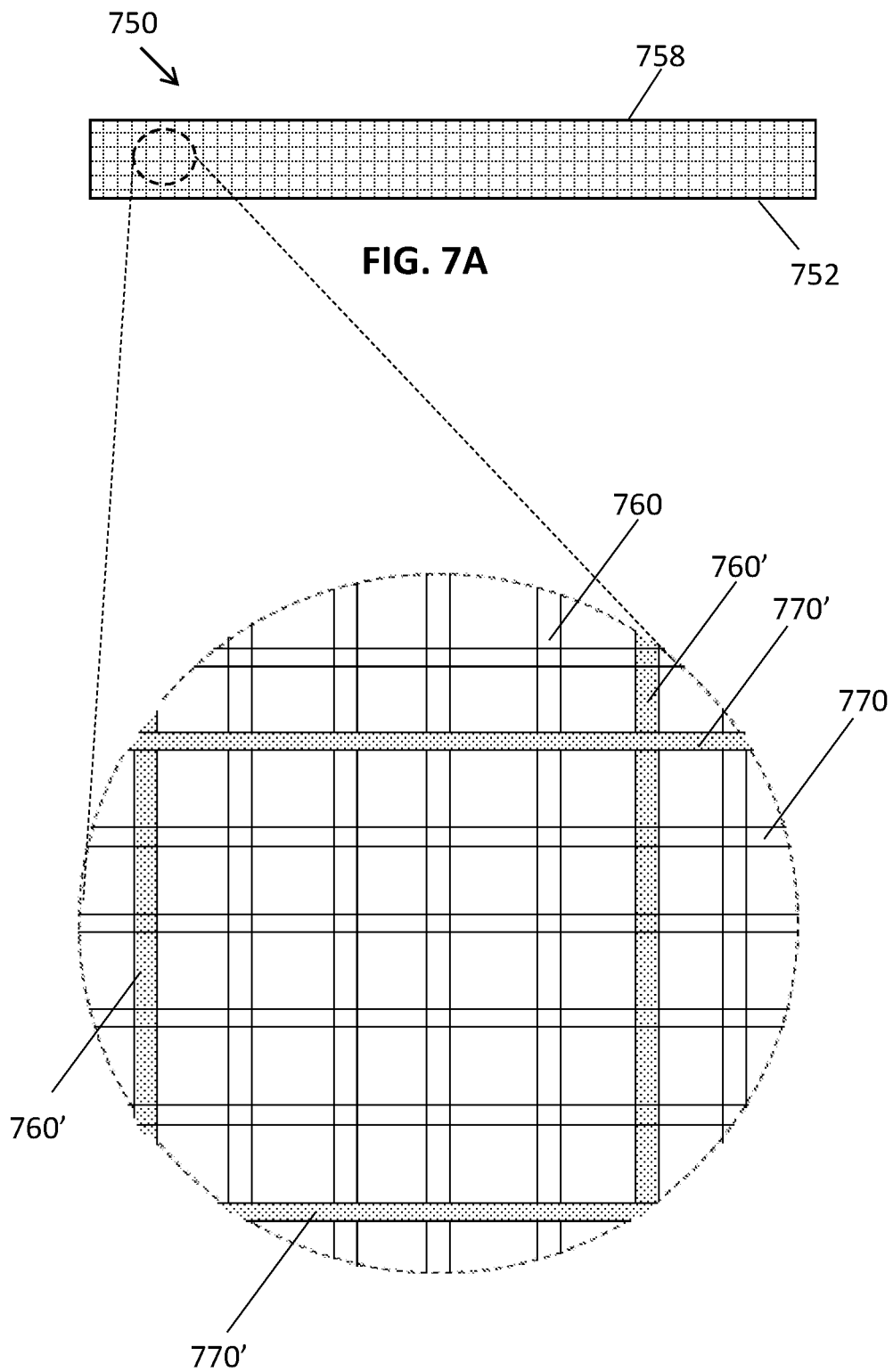
FIG. 7A is a side view of an outer cuff in a flattened condition according to another embodiment of the disclosure.
FIG. 7B is an enlarged view of fibers forming the outer cuff of FIG. 7A.

FIGS. 7A-7B illustrate an outer cuff 750 having a proximal edge 752 and a distal edge 758, the outer cuff being in the form of a fabric comprising first fibers 760 and second fibers 770. Outer cuff 750 may be identical to outer cuffs 550 and 650 described above, with the exception that, instead of having only radiopaque first fibers 560', as in FIG. 5B, or only radiopaque second fibers 670', as in FIG. 6B, outer cuff 750 includes both radiopaque first fibers 760' and radiopaque second fibers 770'. As illustrated, each pair of adjacent radiopaque first fibers 760' are separated by a group of four adjacent or consecutive radiolucent first fibers 760, while each pair of adjacent radiopaque second fibers 770' are separated by a group of four adjacent or consecutive radiolucent second fibers 770. The variations described above in connection with outer cuffs 550, 650 may similarly apply to outer cuff 750. For example, the spacing between adjacent radiopaque first fibers 760' may be smaller than shown, preferably with the individual radiopaque fibers having a relatively small amount of radiopacity, or the spacing between adjacent radiopaque first fibers may be greater than shown, preferably with the individual radiopaque fibers having a relatively large amount of radiopacity. In addition, the spacing between adjacent radiopaque second fibers 770' may be smaller than shown, preferably with the individual radiopaque fibers having a relatively small amount of radiopacity, or the spacing between adjacent radiopaque second fibers may be greater than shown, preferably with the individual radiopaque fibers having a relatively large amount of radiopacity. However, even with the spacing of radiopaque fibers 760' and 770' as shown in FIG. 6B, the radiopacity of the individual radiopaque first and second fibers of outer cuff 750 may preferably be less than the radiopacity of the radiopaque first fibers 560' of outer cuff 550 and less than the radiopacity of the radiopaque second fibers 670' of outer cuff 650. In other words, it may be preferable that the level of radiopacity of any individual radiopaque fiber is dependent not only upon the spacing between adjacent radiopaque fibers having the same orientation, but also on the ratio of the total number of radiopaque fibers (of any orientation) to the total number of fibers (whether radiopaque or radiolucent) forming the fabric of the cuff.

Figures 8A, 8B:
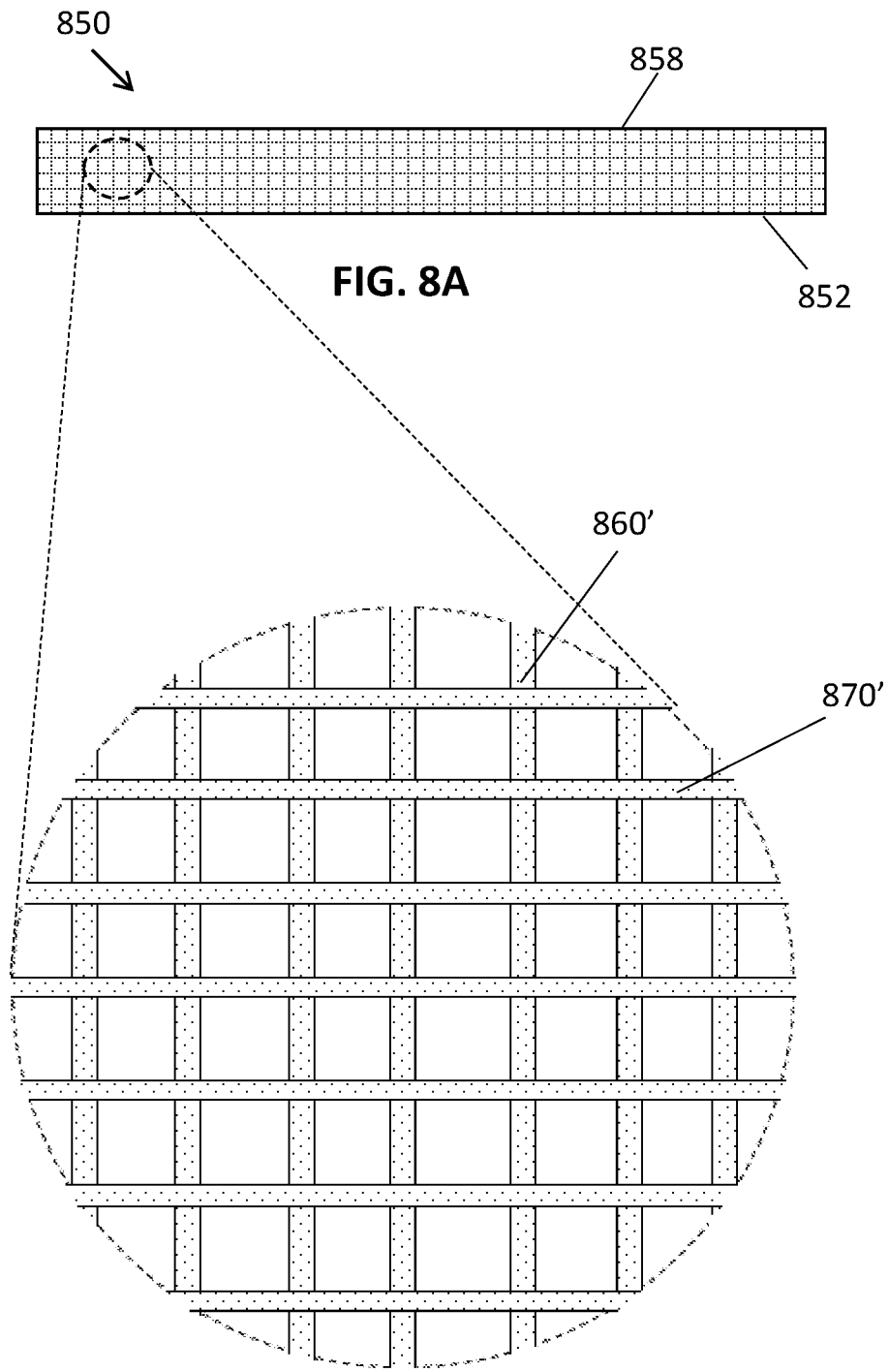
FIG. 8A is a side view of an outer cuff in a flattened condition according to another embodiment of the disclosure.
FIG. 8B is an enlarged view of fibers forming the outer cuff of FIG. 8A.

FIGS. 8A-8B illustrate an outer cuff 850 having a proximal edge 852 and a distal edge 858, the outer cuff being in the form of a fabric comprising first fibers 860' and second fibers 870'. Outer cuff 850 may be identical to outer cuffs 550-750 described above, with the exception that all of the first fibers 860' and the second fibers 870' are radiopaque. In other words, the ratio of the total number of radiopaque fibers of any orientation to the total number of fibers forming the fabric of cuff 850 is equal to one in the illustrated example. Thus, compared to the embodiments of FIGS. 5A-7B, the radiopaque first fibers 860' and radiopaque second fibers 870' preferably have a lower level of radiopacity than any of the radiopaque fibers of outer cuffs 550, 650, and 750. This lower level of radiopacity of radiopaque first fibers 860' and radiopaque second fibers 870' is represented in the drawings with stippling that is less dense than the stippling shown in FIGS. 5B, 6B, and 7B.

Figure 9A:
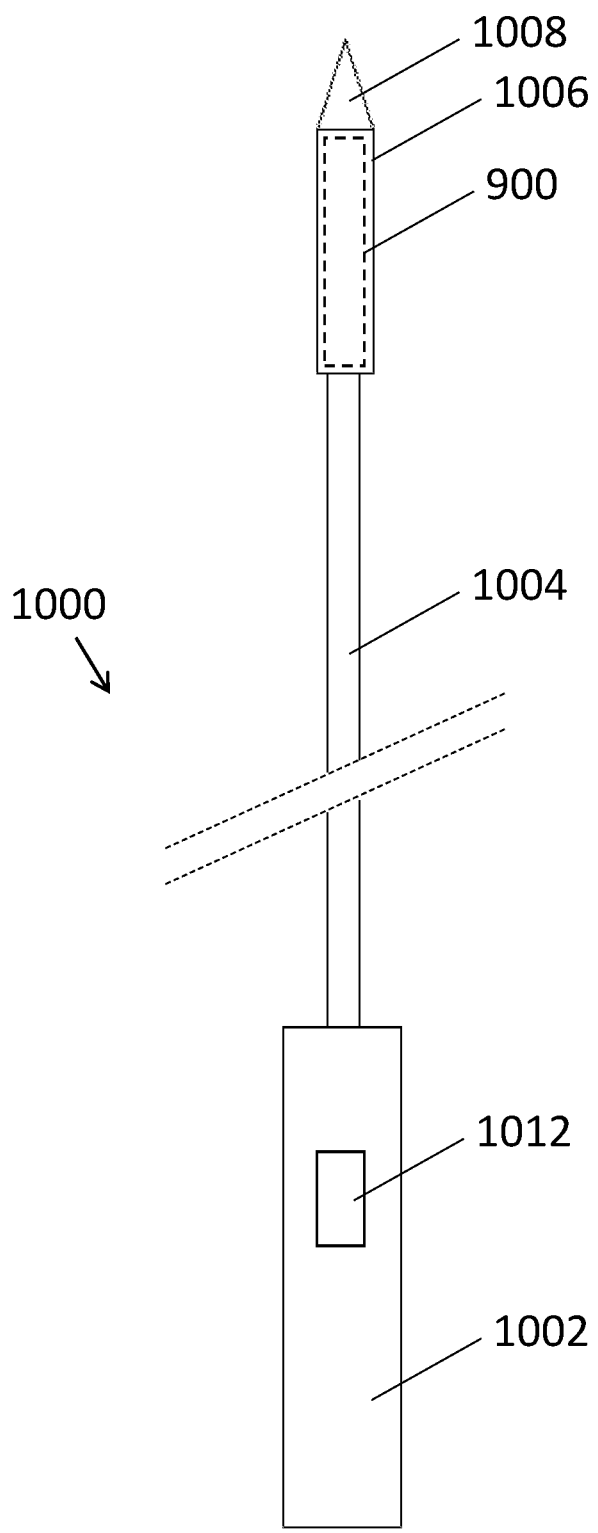
FIGS. 9A-D illustrate steps in a method of implanting a prosthetic heart valve in a patient.

FIG. 9A illustrates a first step of a method of implanting a prosthetic heart valve 900 into a patient according to an aspect of the disclosure. Prosthetic heart valve 900 may incorporate any of the radiopaque outer cuffs described above, including any of outer cuffs 550, 650, 750, and 850, which may have any desired shape such as the shapes of outer cuffs 350 or 450, in conjunction with any of the other prosthetic heart valve features described above, such as the stent 302. In particular, FIG. 9A illustrates prosthetic heart valve 900 having been loaded into a capsule 1006 of a delivery device 1000. Delivery device 1000 may include a handle 1002 and an outer sheath 1004 extending distally therefrom, with the outer sheath being slideable relative to the handle. Outer sheath 1004 may be connected to capsule 1006 near its distal end, the capsule having a larger interior diameter than the outer sheath and being configured to contain prosthetic heart valve 900 in a collapsed condition for delivery into the patient. A distal end of capsule 1006 may be positioned adjacent or may partially surround an atraumatic tip 1008 that may have a generally frustoconical shape. An inner shaft 1010 (best shown in FIG. 9D) may extend from handle 1002, through outer sheath 1004 and capsule 1006, and couple to tip 1008. In the delivery condition shown in FIG. 9A, prosthetic heart valve 900 may be collapsed around inner shaft 1010, and one or both ends of the prosthetic heart valve may be retained in a desired axial and/or rotational position by retaining mechanisms coupled to the inner shaft. Handle 1002 may include a mechanism 1012, for example a deployment wheel, that may be rotated in order to withdraw outer sheath 1004 proximally relative to handle 1002, and thus to draw capsule 1006 proximally away from tip 1008 to uncover prosthetic heart valve 900 and allow it to re-expand once positioned at or near the site of implantation.

Figure 9B:
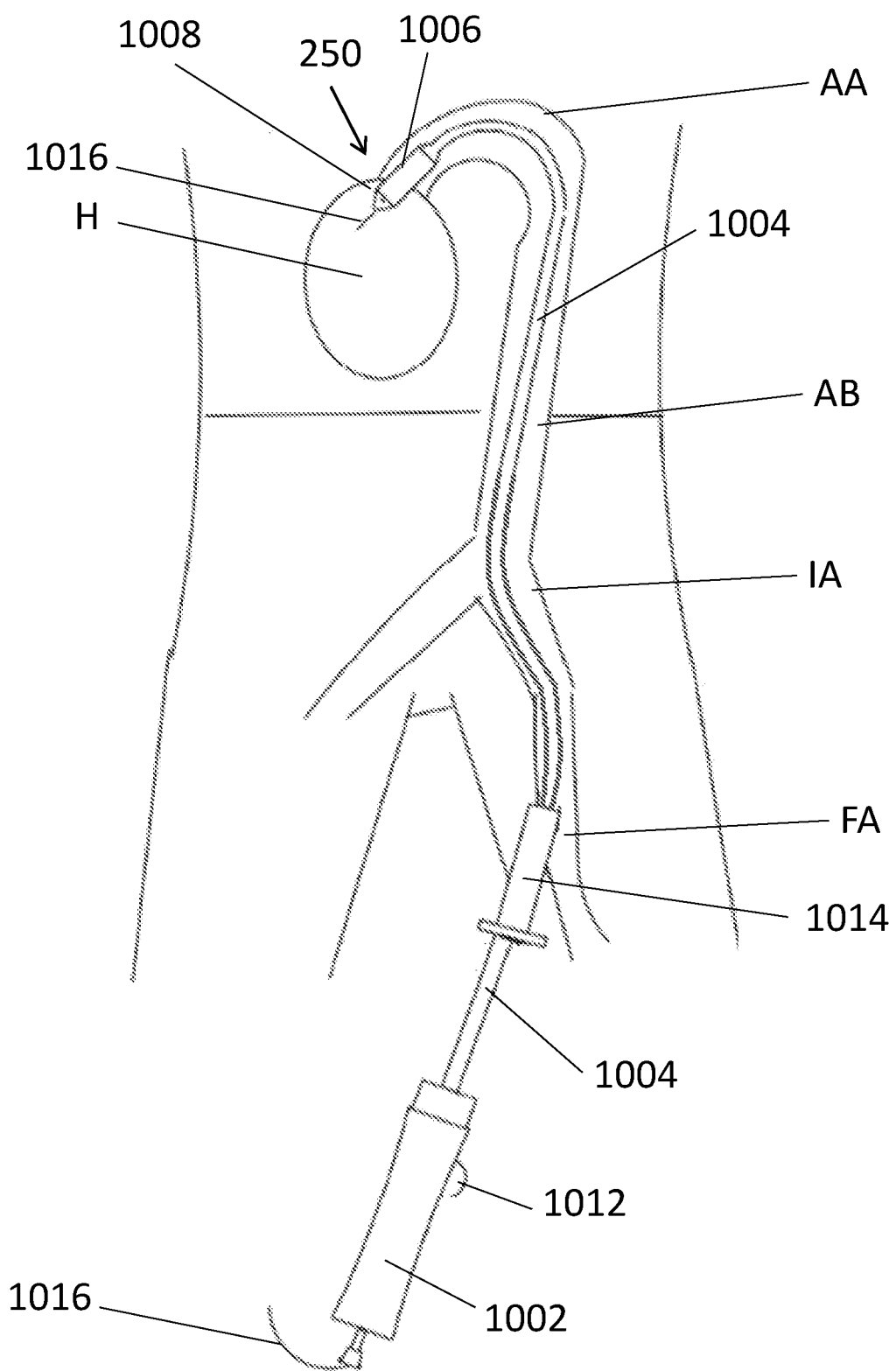

Once prosthetic heart valve 900 is properly loaded into the capsule 1006 of delivery device 1000, as shown in FIG. 9A, the delivery device may be inserted into a patient. FIG. 9B illustrates a second step of the method of implanting prosthetic heart valve 900 into a patient, in this particular example in a native valve annulus 250 such as the native aortic valve annulus in the vicinity of the heart H of the patient. To prepare for performing the method, an introducer 1014 may be inserted into the patient's femoral artery FA through an entry site at the patient's groin using a conventional technique, such as the Seldinger technique. A guidewire 1016 may be inserted through introducer 1014 and advanced through femoral artery FA, iliac artery IA and abdominal aorta AB, around aortic arch AA, and to or through native valve annulus 250. The progress of delivery device 1000 as it passes into femoral artery FA and traverses the patient's vasculature toward native valve annulus 250 may be monitored using imaging, such as fluoroscopy.

Figure 9C:
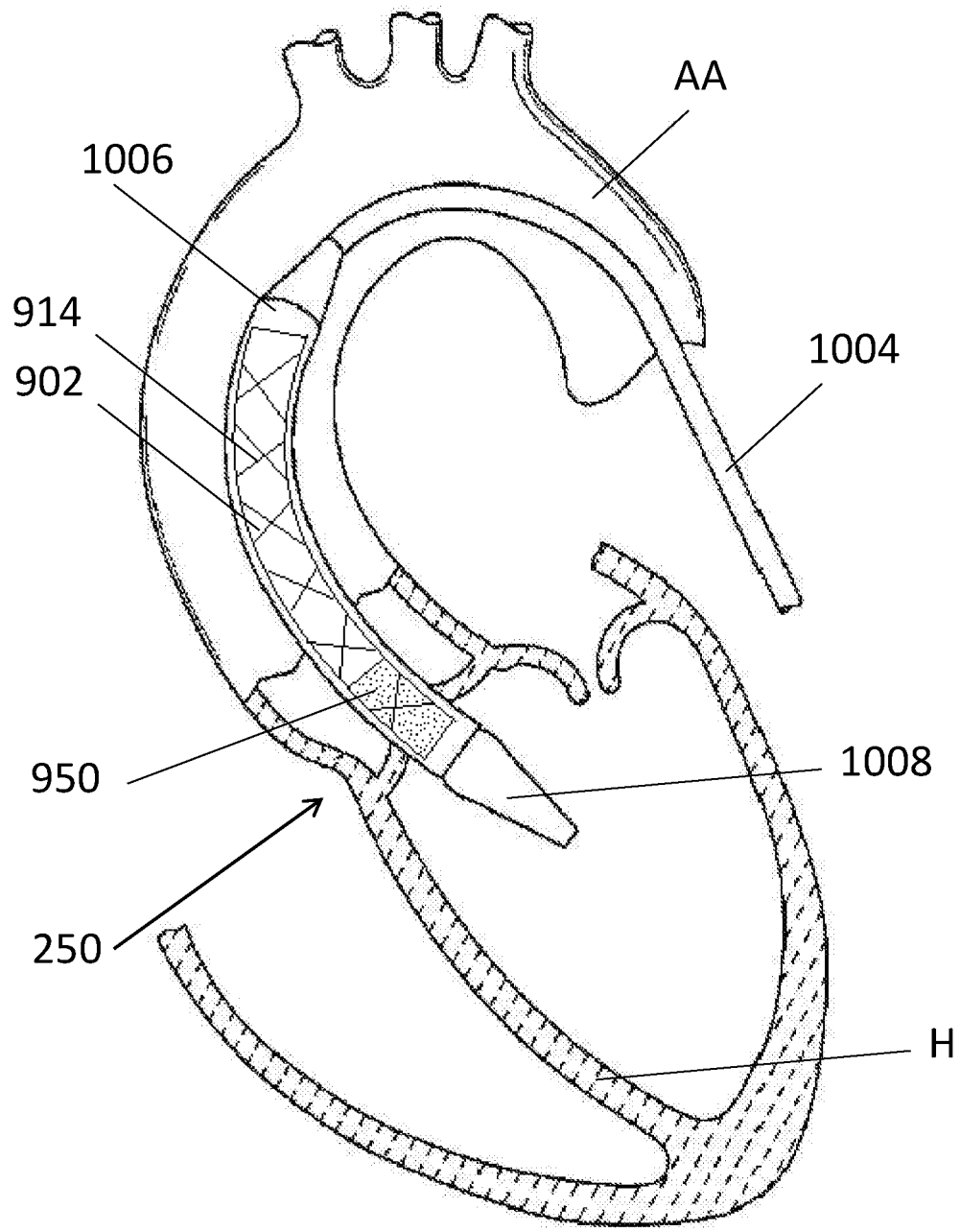

FIG. 9C illustrates an enlarged view of capsule 1006 as tip 1008 passes through native valve annulus 250. Under fluoroscopic guidance, some of the objects illustrated in FIG. 9C may not be visible, or may otherwise appear with minimal contrast compared to the background image displayed on a fluoroscopic imaging display. For example, the structures of the patient's body are not typically distinguishable under fluoroscopic guidance without the use of radiopaque liquid (e.g. contrast) injection or radiopaque markers (e.g. pigtail catheters placed at the native valve annulus 250). The outer sheath 1004, capsule 1006, and tip 1008 are typically partially radiopaque due to the materials of their construction or due to radiopaque markers included therein. As the tip 1008 of delivery device 1000 passes through native valve annulus 250, the physician may be able to visualize the radiopaque outer cuff 950 of prosthetic heart valve 900 while it is collapsed within capsule 1006, as well as the struts 914 of the stent 902 of the prosthetic heart valve. As should be clear from the description above and from FIG. 9C, the radiopacity of outer cuff 950 is preferably great enough so that the outer cuff is readily visible under fluoroscopic guidance, but no so great as to obscure the struts 914 of stent 902 positioned radially inward of the outer cuff. With this configuration, as delivery device 1000 reaches the position shown in FIG. 9C, and the prosthetic heart valve 900 is deployed, the physician or other medical personnel is able to determine the position of both the outer cuff 950 and the stent 902 of prosthetic heart valve 900 (including struts underlying the outer cuff) in relation to native valve annulus 250.

Figure 9D:
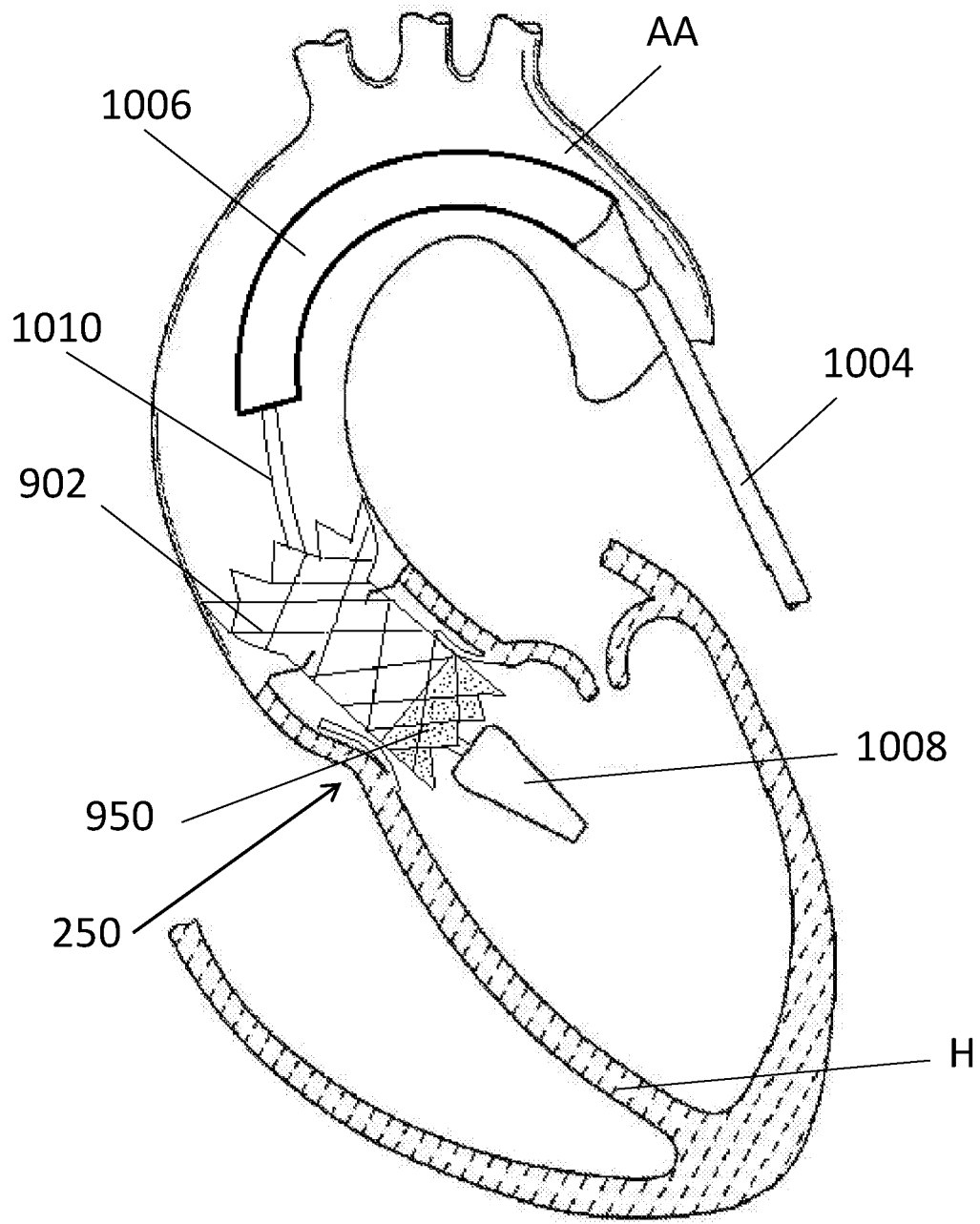

If the physician determines that the position of stent 902 and outer cuff 950 relative to native valve annulus 250 is desirable, the physician may begin to deploy prosthetic heart valve 900 by withdrawing outer sheath 1004 and capsule 1006, for example using mechanism 1012 on handle 1002, to allow the prosthetic heart valve to begin to re-expand within the native valve annulus, as shown in FIG. 9D. It should be understood that, as prosthetic heart valve 900 is deployed from the capsule 1006, any radiopacity of the capsule preferably would not obscure or significantly obscure the physician's ability to visualize the radiopaque outer cuff 950. It should be further be understood that prior to the full release of prosthetic heart valve 900 shown in FIG. 9D, an intermediate stage of release may be encountered in which the annulus section of the prosthetic heart valve, including outer cuff 950 and the prosthetic leaflets of the valve assembly within stent 902, may be expanded and positioned within native valve annulus 250, while the outflow end of the stent is still retained within capsule 1006. In this intermediate stage of deployment, the functionality of prosthetic heart valve 900 may be tested, and a desired positioning of stent 902 and outer cuff 950 relative to native valve annulus 250 may be confirmed via fluoroscopy. If the functionality or positioning of prosthetic heart valve 900 is determined not satisfactory, the prosthetic heart valve may be resheathed into capsule 1006 by advancing outer sheath 1004 distally, for example by using mechanism 1012 on handle 1002, at which point the prosthetic heart valve may be repositioned and deployment may be attempted again.

After prosthetic heart valve 900 is fully released from delivery device 1000, tip 1008 may be pulled proximally through the expanded prosthetic heart valve and into contact with the distal end of outer sheath 1004, and delivery device 1000 and any accessory components may be removed from the patient, completing the procedure.

According to one aspect of the disclosure, a prosthetic heart valve for replacing a native valve comprises:
  a stent having a plurality of struts, an inflow end, an outflow end, a collapsed condition and an expanded condition;
  a valve assembly disposed within the stent;
  a first cuff annularly disposed adjacent the stent; and
  a second cuff having a proximal end adjacent the inflow end of the stent and a distal end spaced apart from the proximal end, the second cuff being annularly disposed about the stent radially outward of the first cuff and radially outward of the stent;

wherein the second cuff is at least partly radiopaque; and/or the first cuff is radiolucent; and/or the plurality of struts is radiopaque, the second cuff being less radiopaque than the plurality of struts; and/or the second cuff is formed of a fabric that includes a plurality of first fiber portions extending in a first fiber direction and a plurality of second fiber portions extending in a second fiber direction; and/or each of the first fiber portions is radiolucent and at least one of the second fiber portions is radiopaque; and/or a multiplicity of the second fiber portions is radiopaque, each of the radiopaque second fiber portions being separated from an adjacent one of the radiopaque second fiber portions by at least one radiolucent second fiber portion; and/or the first fiber direction is substantially orthogonal to the second fiber direction; and/or the stent has a central longitudinal axis extending between the inflow end and the outflow end, the first fiber direction and second fiber direction both being oblique to the central longitudinal axis; and/or the stent has a central longitudinal axis extending between the inflow end and the outflow end, one of the first fiber direction and second fiber direction being orthogonal to the central longitudinal axis; and/or at least one of the first fiber portions is radiopaque and at least one of the second fiber portions is radiopaque; and/or a multiplicity of the first fiber portions is radiopaque, and a multiplicity of the second fiber portions is radiopaque; and/or all of the first fiber portions are radiopaque and all of the second fiber portions are radiopaque; and/or each of the radiopaque first fiber portions is separated from an adjacent one of the radiopaque first fiber portions by at least one radiolucent first fiber portion, and each of the radiopaque second fiber portions is separated from an adjacent one of the radiopaque second fiber portions by at least one radiolucent second fiber portion; and/or the first fiber direction is substantially orthogonal to the second fiber direction; and/or the fabric of the second cuff includes barium sulfate or bismuth trioxide.

According to another aspect of the disclosure, a method of implanting a prosthetic heart valve into a native valve annulus of a patient comprises:

delivering the prosthetic heart valve to the native valve annulus while the prosthetic heart valve is maintained in a collapsed condition within a sheath of a delivery device, the prosthetic heart valve including a stent having a plurality of struts, a first cuff, and a second cuff positioned radially outward of the first cuff and the stent;

imaging the native valve annulus using fluoroscopy while the prosthetic heart valve is positioned adjacent the native valve annulus;

determining a position of the second cuff relative to the native valve annulus using fluoroscopy; and releasing the prosthetic heart valve from the delivery device and deploying the prosthetic heart valve into the native valve annulus; and/or determining positions of selected ones of the plurality of struts relative to the native valve annulus using fluoroscopy, the selected ones of the plurality of struts being positioned radially inward of the second cuff; and/or a radiopacity of the selected ones of the plurality of struts is greater than a radiopacity of the second cuff; and/or the determining step is performed prior to the releasing step; and/or the determining step is performed at least once prior to beginning the releasing step and at least once after beginning releasing step.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, features of one embodiment described above may be combined with features of other embodiments described above.

The invention claimed is:

1. A prosthetic heart valve for replacing a native valve, comprising:
   a stent having a plurality of struts, an inflow end, an outflow end, a collapsed condition and an expanded condition;
   a valve assembly disposed within the stent;
   a first cuff annularly disposed adjacent the stent; and
   a second cuff having a proximal end adjacent the inflow end of the stent and a distal end spaced apart from the proximal end, the second cuff being annularly disposed about the stent radially outward of the first cuff and radially outward of the stent;
   wherein the second cuff overlaps with the first cuff along a longitudinal direction of the stent, thereby creating a space between the first cuff and the second cuff configured to receive retrograde blood flow therewithin, and
   wherein the second cuff is at least partly radiopaque, the second cuff being formed of a fabric that includes a plurality of first fiber portions extending in a first fiber direction and a plurality of second fiber portions extending in a second fiber direction, each of the first fiber portions is radiolucent and at least one of the second fiber portions is radiopaque,
   wherein the plurality of struts includes a plurality of radiopaque struts, the second cuff being less radiopaque than the plurality of radiopaque struts;
   wherein a radiopacity of the second cuff is configured, based on a spacing of radiopaque fibers of the second cuff, to be less radiopaque than the plurality of radiopaque struts; and
   wherein the proximal end of the second cuff is coupled to the stent by sutures.

2. The prosthetic heart valve of claim 1, wherein the first cuff is radiolucent.

3. The prosthetic heart valve of claim 1, wherein a multiplicity of the second fiber portions is radiopaque, each of the radiopaque second fiber portions being separated from an adjacent one of the radiopaque second fiber portions by at least one radiolucent second fiber portion.

4. The prosthetic heart valve of claim 1, wherein the first fiber direction is substantially orthogonal to the second fiber direction.

5. The prosthetic heart valve of claim 4, wherein the stent has a central longitudinal axis extending between the inflow end and the outflow end, the first fiber direction and second fiber direction both being oblique to the central longitudinal axis.

6. The prosthetic heart valve of claim 4, wherein the stent has a central longitudinal axis extending between the inflow end and the outflow end, one of the first fiber direction and second fiber direction being orthogonal to the central longitudinal axis.

7. The prosthetic heart valve of claim 1, wherein the fabric of the second cuff includes barium sulfate or bismuth trioxide.

\* \* \* \* \*